United States Patent
Merchant et al.

(10) Patent No.: US 9,045,536 B2
(45) Date of Patent: Jun. 2, 2015

(54) CELL LINE 3M

(75) Inventors: Ankit A. Merchant, Old Bridge, NJ (US); Yung-Shyeng Tsao, Summit, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 403 days.

(21) Appl. No.: 13/517,901

(22) PCT Filed: Dec. 16, 2010

(86) PCT No.: PCT/US2010/060653
§ 371 (c)(1),
(2), (4) Date: Jun. 20, 2012

(87) PCT Pub. No.: WO2011/079004
PCT Pub. Date: Jun. 30, 2011

(65) Prior Publication Data
US 2012/0264170 A1    Oct. 18, 2012

Related U.S. Application Data

(60) Provisional application No. 61/289,703, filed on Dec. 23, 2009.

(51) Int. Cl.
| | |
|---|---|
| C12P 21/00 | (2006.01) |
| C12P 21/02 | (2006.01) |
| C12P 21/08 | (2006.01) |
| C12N 5/10 | (2006.01) |
| C07K 16/24 | (2006.01) |
| C07K 16/22 | (2006.01) |
| C12N 5/09 | (2010.01) |

(52) U.S. Cl.
CPC .............. *C07K 16/244* (2013.01); *C07K 16/22* (2013.01); *C07K 2317/14* (2013.01); *C12N 5/0693* (2013.01); *C12N 2510/02* (2013.01); *C12N 2500/92* (2013.01); *C12N 2501/33* (2013.01)

(58) Field of Classification Search
None
See application file for complete search history.

(56) References Cited

FOREIGN PATENT DOCUMENTS

EP    1221476 B1    1/2008

OTHER PUBLICATIONS

Sinacore MS1, Charlebois TS, Harrison S, Brennan S, Richards T, Hamilton M, Scott S, Brodeur S, Oakes P, Leonard M, Switzer M, Anagnostopoulos A, Foster B, Harris A, Jankowski M, Bond M, Martin S, Adamson SR.CHO DUKX cell lineages preadapted to growth in serum-free suspension culture enable rapid development of cell culture processes for the manufacture of recombinant proteins. Biotechnol Bioeng. Nov. 20, 1996;52(4):518-28.
Al-Rubeai. Development of Cell Lines for Controlled Proliferation and Apoptosis. University College Dublin (online). Aug. 2009 (retrieved on Jan. 31, 2011). Retrieved from the internet URL:<http://www.ucd.ie/ccerc/PowerPoinVCell%20line%20development%201BC.ppl>.
Product Code C 5467. SIGMA (online) Apr. 2005 (publication date: Apr. 2005 on p. 2) [retrieved on Jan. 31, 2011]. Retrieved from the internet URL:<hllp://www.sigmaaldrich.com/etclmedialib/docs/Sigma/DatasheeV3/c5467dat.Par.0001.File.tmp/c5467dat.pdf>.
Rasmussen B, Davis R, Thomas J, Reddy P. Isolation, characterization and recombinant protein expression in Veggie-CHO: A serum-free CHO host cell line. Cytotechnology. Nov. 1998;28(1-3):31-42.
Shroder et al. Serum- and protein-free media formulations for the Chinese hamster ovary cell line DUKXB11. Journal of Biotechnology.2004 vol. 108 pp. 279-292. Abstract. PowerPoint Index. University College Dublin (online) Aug. 2009 [retrieved on Feb. 8, 2011].
Birch JR1, Racher AJ. Antibody production. Adv Drug Deliv Rev. Aug. 7, 2006;58(5-6):671-85. Epub May 22, 2006.
Sinacore et al. Adaptation of Mammalian Cells to Growth in Serum-Free Media. From: Methods in Biotechnology, vol. 8: Animal Cell Biotechnology, pp. 11-22. 1999, see p. 16-18.
PowerPoint Index. University College Dublin (online) Aug. 2009 [retrieved on Feb. 8, 2011]. Retrieved from the internet URL:<http:/1www.ucd.ie/ccerc/PowerPoinV>. see line 2 'Cell line developmen . . . > Aug. 11, 2009 17:35 7.4M', which refers (links) to the Al-Rubeai document and provides its publication date ('Last Modified' date).
Renate Kunert, Johannes Gach, Hermann Katinger. Expression of a Fab Fragment in CHO and *Pichia pastoris*—A Comparative Case Study. Bioprocess International 6 (S6): 34-40 (2008).
Lattenmayer et al. Protein-free transfection of CHO host cells with an IgG-fusion protein: selection and characterization of stable high producers and comparison to conventionally transfected clones. Biotechnol Bioeng. 96(6):1118-1126 (2007).
Kunert et al. CHO-recombinant human growth hormone as a protease sensitive reporter protein.Appl Microbiol Biotechnol. Sep. 2009;84(4):693-699 Epub Apr. 25, 2009.

*Primary Examiner* — Karen Canella

(57) ABSTRACT

The present invention provides, inter alia, an isolated cell line, 3M as well as methods for making such a cell line and methods of using such a cell line, e.g., to produce a protein such as an immunoglobulin.

20 Claims, 4 Drawing Sheets

SEQUENCE LISTING

```
<160> NUMBER OF SEQ ID NOS: 104

<210> SEQ ID NO 1
<211> LENGTH: 128
<212> TYPE: PRT
<213> ORGANISM: Homo sapiens

<400> SEQUENCE: 1

Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
```

```
                    85                  90                  95
Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
            115                 120                 125

<210> SEQ ID NO 2
<211> LENGTH: 137
<212> TYPE: PRT
<213> ORGANISM: Homo sapiens

<400> SEQUENCE: 2

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 3
<211> LENGTH: 128
<212> TYPE: PRT
<213> ORGANISM: Homo sapiens

<400> SEQUENCE: 3

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
            115                 120                 125

<210> SEQ ID NO 4
<211> LENGTH: 128
<212> TYPE: PRT
```

<213> ORGANISM: Homo sapiens

<400> SEQUENCE: 4

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 5
<211> LENGTH: 128
<212> TYPE: PRT
<213> ORGANISM: Homo sapiens

<400> SEQUENCE: 5

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 6
<211> LENGTH: 128
<212> TYPE: PRT
<213> ORGANISM: Homo sapiens

<400> SEQUENCE: 6

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

```
Leu Leu Ile Lys Tyr Ala Ser Gln Ser Leu Ser Gly Ile Pro Asp Arg
 65                  70                  75                  80

Phe Ser Gly Ser Gly Ser Gly Thr Asp Phe Thr Leu Thr Ile Ser Arg
                 85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 7
<211> LENGTH: 137
<212> TYPE: PRT
<213> ORGANISM: Homo sapiens

<400> SEQUENCE: 7

```
Met Glu Phe Gly Leu Ser Trp Val Phe Leu Val Ala Ile Leu Lys Gly
  1               5                  10                  15

Val Gln Cys Glu Val Gln Leu Val Gln Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Ser Phe Ala Met His Trp Val Arg Gln Ala Pro Gly Lys Gly Leu
     50                  55                  60

Glu Trp Ile Ser Val Ile Asp Thr Arg Gly Ala Thr Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 8
<211> LENGTH: 137
<212> TYPE: PRT
<213> ORGANISM: Homo sapiens

<400> SEQUENCE: 8

```
Met Glu Phe Gly Leu Ser Trp Val Phe Leu Val Ala Ile Leu Lys Gly
  1               5                  10                  15

Val Gln Cys Glu Val Gln Leu Val Gln Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Phe Ala Met His Trp Val Arg Gln Ala Pro Gly Lys Gly Leu
     50                  55                  60

Glu Trp Ile Ser Val Ile Asp Thr Arg Gly Ala Thr Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125
```

Gln Gly Thr Thr Val Thr Val Ser Ser
    130                 135

<210> SEQ ID NO 9
<211> LENGTH: 16
<212> TYPE: PRT
<213> ORGANISM: Artificial Sequence
<220> FEATURE:
<223> OTHER INFORMATION: CDR

<400> SEQUENCE: 9

Lys Ala Ser Lys Lys Val Thr Ile Phe Gly Ser Ile Ser Ala Leu His
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: CDR

<400> SEQUENCE: 10

Asn Gly Ala Lys Leu Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: CDR

<400> SEQUENCE: 11

Leu Gln Asn Lys Glu Val Pro Tyr Thr
1               5

<210> SEQ ID NO 12
<211> LENGTH: 5
<212> TYPE: PRT
<213> ORGANISM: Artificial Sequence
<220> FEATURE:
<223> OTHER INFORMATION: CDR

<400> SEQUENCE: 12

Ser Tyr Gly Ile Thr
1               5

<210> SEQ ID NO 13
<211> LENGTH: 17
<212> TYPE: PRT
<213> ORGANISM: Artificial Sequence
<220> FEATURE:
<223> OTHER INFORMATION: CDR

<400> SEQUENCE: 13

Glu Asn Tyr Pro Arg Ser Gly Asn Thr Tyr Tyr Asn Glu Lys Phe Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: CDR

```
<400> SEQUENCE: 14

Cys Glu Phe Ile Ser Thr Val Val Ala Pro Tyr Tyr Tyr Ala Leu Asp
1               5                   10                  15

Tyr

<210> SEQ ID NO 15
<211> LENGTH: 17
<212> TYPE: PRT
<213> ORGANISM: Artificial Sequence
<220> FEATURE:
<223> OTHER INFORMATION: CDR

<400> SEQUENCE: 15

Ser Glu Phe Ile Ser Thr Val Val Ala Pro Tyr Tyr Tyr Ala Leu Asp
1               5                   10                  15

Tyr

<210> SEQ ID NO 16
<211> LENGTH: 17
<212> TYPE: PRT
<213> ORGANISM: Artificial Sequence
<220> FEATURE:
<223> OTHER INFORMATION: CDR

<400> SEQUENCE: 16

Ala Glu Phe Ile Ser Thr Val Val Ala Pro Tyr Tyr Tyr Ala Leu Asp
1               5                   10                  15

Tyr

<210> SEQ ID NO 17
<211> LENGTH: 17
<212> TYPE: PRT
<213> ORGANISM: Artificial Sequence
<220> FEATURE:
<223> OTHER INFORMATION: CDR

<400> SEQUENCE: 17

Val Glu Phe Ile Ser Thr Val Val Ala Pro Tyr Tyr Tyr Ala Leu Asp
1               5                   10                  15

Tyr

<210> SEQ ID NO 18
<211> LENGTH: 17
<212> TYPE: PRT
<213> ORGANISM: Artificial Sequence
<220> FEATURE:
<223> OTHER INFORMATION: CDR

<400> SEQUENCE: 18

Ser Glu Phe Ile Ser Thr Val Met Ala Pro Tyr Tyr Tyr Ala Leu Asp
1               5                   10                  15

Tyr

<210> SEQ ID NO 19
<211> LENGTH: 17
<212> TYPE: PRT
<213> ORGANISM: Artificial Sequence
<220> FEATURE:
<223> OTHER INFORMATION: CDR

<400> SEQUENCE: 19

Ser Glu Phe Thr Ser Thr Val Val Ala Pro Tyr Tyr Tyr Ala Leu Asp
1               5                   10                  15
```

Tyr

<210> SEQ ID NO 20
<211> LENGTH: 108
<212> TYPE: PRT
<213> ORGANISM: Artificial Sequence
<220> FEATURE:
<223> OTHER INFORMATION: Ig light chain

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ile Pro Phe
                85                  90                  95

Thr Phe Gly Gln Gly Thr Lys Val Glu Ile Lys Arg
            100                 105
```

<210> SEQ ID NO 21
<211> LENGTH: 116
<212> TYPE: PRT
<213> ORGANISM: Artificial Sequence
<220> FEATURE:
<223> OTHER INFORMATION: Ig heavy chain

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Phe Ala Tyr Trp Gly Gln Gly Thr Leu Val
            100                 105                 110

Thr Val Ser Ser
        115
```

<210> SEQ ID NO 22
<211> LENGTH: 116
<212> TYPE: PRT
<213> ORGANISM: Artificial Sequence
<220> FEATURE:
<223> OTHER INFORMATION: Ig heavy chain

<400> SEQUENCE: 22

```
Gln Val Gln Leu Val Gln Ser Gly Ala Glu Val Lys Lys Pro Gly Ala
```

```
                1               5                  10                 15
            Ser Val Lys Val Ser Cys Lys Ala Ser Gly Tyr Ile Phe Ile Thr Tyr
                            20                  25                 30
            Trp Met Thr Trp Val Arg Gln Ala Pro Gly Gln Gly Leu Glu Trp Met
                        35                  40                  45
            Gly Gln Ile Phe Pro Ala Ser Gly Ser Ala Asp Tyr Ala Gln Lys Leu
                    50                  55                  60
            Gln Gly Arg Val Thr Met Thr Thr Asp Thr Ser Thr Ser Thr Ala Tyr
             65                 70                  75                  80
            Met Glu Leu Arg Ser Leu Arg Ser Asp Asp Thr Ala Val Tyr Tyr Cys
                            85                  90                  95
            Ala Arg Gly Gly Gly Gly Phe Ala Tyr Trp Gly Gln Gly Thr Leu Val
                        100                 105                 110
            Thr Val Ser Ser
                    115
```

<210> SEQ ID NO 23
<211> LENGTH: 10
<212> TYPE: PRT
<213> ORGANISM: Artificial Sequence
<220> FEATURE:
<223> OTHER INFORMATION: CDR

<400> SEQUENCE: 23

```
            Gly Phe Thr Phe Ser Ser Tyr Thr Met Ser
             1               5                  10
```

<210> SEQ ID NO 24
<211> LENGTH: 17
<212> TYPE: PRT
<213> ORGANISM: Artificial Sequence
<220> FEATURE:
<223> OTHER INFORMATION: CDR

<400> SEQUENCE: 24

```
            Thr Ile Ser Ser Gly Gly Thr Tyr Thr Tyr Tyr Pro Asp Ser Val Lys
             1               5                  10                  15
            Gly
```

<210> SEQ ID NO 25
<211> LENGTH: 13
<212> TYPE: PRT
<213> ORGANISM: Artificial Sequence
<220> FEATURE:
<223> OTHER INFORMATION: CDR

<400> SEQUENCE: 25

```
            Asp Asn His Ala Tyr Asp Arg Gly Pro Phe Phe Asp Tyr
             1               5                  10
```

<210> SEQ ID NO 26
<211> LENGTH: 17
<212> TYPE: PRT
<213> ORGANISM: Artificial Sequence
<220> FEATURE:
<223> OTHER INFORMATION: CDR

<400> SEQUENCE: 26

```
            Lys Ser Ser Gln Asn Leu Phe Tyr Arg Ser Asn Gln Lys Asn His Leu
             1               5                  10                  15
            Ala
```

```
<210> SEQ ID NO 27
<211> LENGTH: 7
<212> TYPE: PRT
<213> ORGANISM: Artificial Sequence
<220> FEATURE:
<223> OTHER INFORMATION: CDR

<400> SEQUENCE: 27

Trp Thr Ser Thr Arg Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: CDR

<400> SEQUENCE: 28

Gln Gln Tyr Tyr Ser Tyr Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: CDR

<400> SEQUENCE: 29

Ala Tyr Gly Met Asp
1               5

<210> SEQ ID NO 30
<211> LENGTH: 17
<212> TYPE: PRT
<213> ORGANISM: Artificial Sequence
<220> FEATURE:
<223> OTHER INFORMATION: CDR

<400> SEQUENCE: 30

Ser Ile Ser Pro Ser Gly Gly Arg Thr Lys Tyr Ala Asp Ser Val Lys
1               5                   10                  15

Gly

<210> SEQ ID NO 31
<211> LENGTH: 14
<212> TYPE: PRT
<213> ORGANISM: Artificial Sequence
<220> FEATURE:
<223> OTHER INFORMATION: CDR

<400> SEQUENCE: 31

Asp Leu Gly Gly Gly Tyr Tyr Tyr Tyr Gly Met Asp Val
1               5                   10

<210> SEQ ID NO 32
<211> LENGTH: 14
<212> TYPE: PRT
<213> ORGANISM: Artificial Sequence
<220> FEATURE:
<223> OTHER INFORMATION: CDR

<400> SEQUENCE: 32

Thr Gly Thr Ser Ser Asp Val Gly Gly Tyr Asn Tyr Val Ser
1               5                   10
```

<210> SEQ ID NO 33
<211> LENGTH: 7
<212> TYPE: PRT
<213> ORGANISM: Artificial Sequence
<220> FEATURE:
<223> OTHER INFORMATION: CDR

<400> SEQUENCE: 33

Glu Val Ser Asn Arg Pro Ser
1               5

<210> SEQ ID NO 34
<211> LENGTH: 12
<212> TYPE: PRT
<213> ORGANISM: Artificial Sequence
<220> FEATURE:
<223> OTHER INFORMATION: CDR

<400> SEQUENCE: 34

Ser Ser Tyr Thr Ser Ser Ser Thr Leu Phe Tyr Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CDR

<400> SEQUENCE: 35

Gly Lys Thr Phe Trp Ser Trp Gly Ile Asn
1               5                   10

<210> SEQ ID NO 36
<211> LENGTH: 17
<212> TYPE: PRT
<213> ORGANISM: Artificial Sequence
<220> FEATURE:
<223> OTHER INFORMATION: CDR

<400> SEQUENCE: 36

Tyr Ile Tyr Ile Gly Thr Gly Tyr Thr Glu Pro Asn Pro Lys Tyr Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: CDR

<400> SEQUENCE: 37

Ile Gly Gly Tyr Tyr Gly Asn Phe Ala Asp
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CDR

<400> SEQUENCE: 38

Ile Gly Gly Tyr Tyr Gly Asn Phe Asp Gln

<210> SEQ ID NO 39
<211> LENGTH: 16
<212> TYPE: PRT
<213> ORGANISM: Artificial Sequence
<220> FEATURE:
<223> OTHER INFORMATION: CDR

<400> SEQUENCE: 39

Arg Ser Ser Gln Ser Leu Leu Ile Ser Gly Gly Asn Thr Tyr Leu Asn
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: CDR

<400> SEQUENCE: 40

Leu Val Ser Lys Leu Asp Gln
1               5

<210> SEQ ID NO 41
<211> LENGTH: 9
<212> TYPE: PRT
<213> ORGANISM: Artificial Sequence
<220> FEATURE:
<223> OTHER INFORMATION: CDR

<400> SEQUENCE: 41

Trp Gln Gly Thr Tyr Phe Pro Leu Thr
1               5

<210> SEQ ID NO 42
<211> LENGTH: 114
<212> TYPE: PRT
<213> ORGANISM: Artificial Sequence
<220> FEATURE:
<223> OTHER INFORMATION: Ig light chain

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Phe Ser
                20                  25                  30

Glu Asn Gln Lys Asn Tyr Leu Ala Trp Tyr Leu Gln Lys Pro Gly Gln
            35                  40                  45

Ser Pro Gln Leu Leu Ile Tyr Trp Thr Ser Thr Arg Gln Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Tyr Thr Pro Tyr Thr Phe Gly Gln Gly Thr Lys Val Glu Ile
            100                 105                 110

Lys Arg

<210> SEQ ID NO 43
<211> LENGTH: 124
<212> TYPE: PRT
<213> ORGANISM: Artificial Sequence
<220> FEATURE:
<223> OTHER INFORMATION: Ig heavy chain

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Pro Ser His
            20                  25                  30

Ser Val Ser Trp Ile Arg Gln Pro Pro Gly Lys Gly Leu Glu Trp Ile
        35                  40                  45

Gly Ile Ile Trp Asn Gln Gly Gly Thr Asp Tyr Asn Ser Ala Phe Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Ala Tyr Ile Thr Asp Tyr Tyr Tyr Glu Asn Tyr Phe Met Asp
            100                 105                 110

Ala Trp Gly Gln Gly Thr Leu Val Thr Val Ser Ser
        115                 120

<210> SEQ ID NO 44
<211> LENGTH: 5
<212> TYPE: PRT
<213> ORGANISM: Artificial Sequence
<220> FEATURE:
<223> OTHER INFORMATION: CDR

<400> SEQUENCE: 44

Thr Tyr Trp Met His
1               5

<210> SEQ ID NO 45
<211> LENGTH: 5
<212> TYPE: PRT
<213> ORGANISM: Artificial Sequence
<220> FEATURE:
<223> OTHER INFORMATION: CDR

<400> SEQUENCE: 45

Thr Tyr Trp Met His
1               5

<210> SEQ ID NO 46
<211> LENGTH: 17
<212> TYPE: PRT
<213> ORGANISM: Artificial Sequence
<220> FEATURE:
<223> OTHER INFORMATION: CDR

<400> SEQUENCE: 46

Glu Ile Asn Pro Thr Asn Gly His Thr Asn Tyr Asn Glu Lys Phe Lys
1               5                   10                  15

Ser

<210> SEQ ID NO 47
<211> LENGTH: 17
<212> TYPE: PRT
<213> ORGANISM: Artificial Sequence
<220> FEATURE:
<223> OTHER INFORMATION: CDR

<400> SEQUENCE: 47

```
Glu Ile Asn Pro Thr Asn Gly His Thr Asn Tyr Asn Pro Ser Phe Gln
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: CDR

<400> SEQUENCE: 48

Glu Ile Asn Pro Thr Asn Gly His Thr Asn Tyr Asn Gln Lys Phe Gln
1               5                   10                  15

Gly

<210> SEQ ID NO 49
<211> LENGTH: 9
<212> TYPE: PRT
<213> ORGANISM: Artificial Sequence
<220> FEATURE:
<223> OTHER INFORMATION: CDR

<400> SEQUENCE: 49

Asn Tyr Val Gly Ser Ile Phe Asp Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: CDR

<400> SEQUENCE: 50

Asn Tyr Val Gly Ser Ile Phe Asp Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: CDR

<400> SEQUENCE: 51

Lys Ala Ser Glu Asn Val Val Ser Tyr Val Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: CDR

<400> SEQUENCE: 52

Lys Ala Ser Glu Asn Val Val Ser Tyr Val Ser
1               5                   10

<210> SEQ ID NO 53
<211> LENGTH: 7
<212> TYPE: PRT
<213> ORGANISM: Artificial Sequence
<220> FEATURE:
```

```
<223> OTHER INFORMATION: CDR

<400> SEQUENCE: 53

Gly Ala Ser Asn Arg Asn Thr
1               5

<210> SEQ ID NO 54
<211> LENGTH: 7
<212> TYPE: PRT
<213> ORGANISM: Artificial Sequence
<220> FEATURE:
<223> OTHER INFORMATION: CDR

<400> SEQUENCE: 54

Gly Ala Ser Asn Arg Asn Thr
1               5

<210> SEQ ID NO 55
<211> LENGTH: 7
<212> TYPE: PRT
<213> ORGANISM: Artificial Sequence
<220> FEATURE:
<223> OTHER INFORMATION: CDR

<400> SEQUENCE: 55

Gly Ala Ser Asn Arg Glu Ser
1               5

<210> SEQ ID NO 56
<211> LENGTH: 9
<212> TYPE: PRT
<213> ORGANISM: Artificial Sequence
<220> FEATURE:
<223> OTHER INFORMATION: CDR

<400> SEQUENCE: 56

Gly Gln Ser Tyr Asn Tyr Pro Tyr Thr
1               5

<210> SEQ ID NO 57
<211> LENGTH: 9
<212> TYPE: PRT
<213> ORGANISM: Artificial Sequence
<220> FEATURE:
<223> OTHER INFORMATION: CDR

<400> SEQUENCE: 57

Gly Gln Ser Tyr Asn Tyr Pro Tyr Thr
1               5

<210> SEQ ID NO 58
<211> LENGTH: 119
<212> TYPE: PRT
<213> ORGANISM: Artificial Sequence
<220> FEATURE:
<223> OTHER INFORMATION: Ig heavy chain

<400> SEQUENCE: 58

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Arg Asn Tyr
            20                  25                  30

Ala Met Tyr Trp Val Arg Gln Ala Pro Gly Lys Gly Leu Glu Trp Val
        35                  40                  45

Ser Ala Ile Gly Ser Gly Gly Gly Thr Tyr Tyr Ala Asp Ser Val Lys
```

```
                    50                  55                  60
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                     85                  90                  95

Arg Ala Pro Asn Trp Gly Ser Asp Ala Phe Asp Ile Trp Gly Gln Gly
                100                 105                 110

Thr Met Val Thr Val Ser Ser
            115

<210> SEQ ID NO 59
<211> LENGTH: 107
<212> TYPE: PRT
<213> ORGANISM: Artificial Sequence
<220> FEATURE:
<223> OTHER INFORMATION: Ig light chain

<400> SEQUENCE: 59

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                     85                  90                  95

Thr Phe Gly Pro Gly Thr Lys Val Asp Ile Lys
                100                 105

<210> SEQ ID NO 60
<211> LENGTH: 118
<212> TYPE: PRT
<213> ORGANISM: Artificial Sequence
<220> FEATURE:
<223> OTHER INFORMATION: Ig heavy chain

<400> SEQUENCE: 60

Gln Val Glu Leu Val Glu Ser Gly Gly Gly Val Val Gln Pro Gly Arg
  1               5                  10                  15

Ser Gln Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Ile Ile Trp Phe Asp Gly Ser Ser Thr Tyr Tyr Ala Asp Ser Val
         50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                     85                  90                  95

Ala Arg Glu Leu Gly Arg Arg Tyr Phe Asp Leu Trp Gly Arg Gly Thr
                100                 105                 110

Leu Val Ser Val Ser Ser
            115
```

```
<210> SEQ ID NO 61
<211> LENGTH: 108
<212> TYPE: PRT
<213> ORGANISM: Artificial Sequence
<220> FEATURE:
<223> OTHER INFORMATION: Ig light chain

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 62
<211> LENGTH: 125
<212> TYPE: PRT
<213> ORGANISM: Artificial Sequence
<220> FEATURE:
<223> OTHER INFORMATION: Ig heavy chain

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser
        115                 120                 125

<210> SEQ ID NO 63
<211> LENGTH: 109
<212> TYPE: PRT
<213> ORGANISM: Artificial Sequence
<220> FEATURE:
<223> OTHER INFORMATION: Ig light chain

<400> SEQUENCE: 63

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
```

```
                    20                  25                  30
Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Cys
                 85                  90                  95

Ser Phe Gly Gln Gly Thr Lys Leu Glu Ile Lys Arg Thr
                100                 105
```

<210> SEQ ID NO 64
<211> LENGTH: 130
<212> TYPE: PRT
<213> ORGANISM: Artificial Sequence
<220> FEATURE:
<223> OTHER INFORMATION: Ig heavy chain

<400> SEQUENCE: 64

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130
```

<210> SEQ ID NO 65
<211> LENGTH: 109
<212> TYPE: PRT
<213> ORGANISM: Artificial Sequence
<220> FEATURE:
<223> OTHER INFORMATION: Ig light chain

<400> SEQUENCE: 65

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Gln Ala Pro Ile Leu Val Ile Tyr
            35                  40                  45

Gly Glu Asn Lys Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80
```

-continued

```
Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105

<210> SEQ ID NO 66
<211> LENGTH: 119
<212> TYPE: PRT
<213> ORGANISM: Artificial Sequence
<220> FEATURE:
<223> OTHER INFORMATION: Ig heavy chain

<400> SEQUENCE: 66

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Thr Gly Arg Thr Asp Ala Phe Asp Ile Trp Gly Gln Gly
            100                 105                 110

Thr Trp Val Thr Val Ser Ser
        115

<210> SEQ ID NO 67
<211> LENGTH: 112
<212> TYPE: PRT
<213> ORGANISM: Artificial Sequence
<220> FEATURE:
<223> OTHER INFORMATION: Ig light chain

<400> SEQUENCE: 67

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

<210> SEQ ID NO 68
<211> LENGTH: 117
<212> TYPE: PRT
<213> ORGANISM: Artificial Sequence
<220> FEATURE:
<223> OTHER INFORMATION: Ig heavy chain
```

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Gly Gly
            20                  25                  30

Tyr Leu Trp Asn Trp Ile Arg Gln Pro Pro Gly Lys Gly Leu Glu Trp
        35                  40                  45

Ile Gly Tyr Ile Ser Tyr Asp Gly Thr Asn Tyr Lys Pro Ser Leu
    50                  55                  60

Lys Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
            100                 105                 110

Val Thr Val Ser Ser
        115

<210> SEQ ID NO 69
<211> LENGTH: 112
<212> TYPE: PRT
<213> ORGANISM: Artificial Sequence
<220> FEATURE:
<223> OTHER INFORMATION: Ig light chain

<400> SEQUENCE: 69

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 70
<211> LENGTH: 110
<212> TYPE: PRT
<213> ORGANISM: Homo sapiens

<400> SEQUENCE: 70

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Tyr Val Tyr Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Ala Thr Trp Asp Asp Ser Leu
                85                  90                  95

Ser Gly Val Val Phe Gly Gly Gly Thr Lys Val Thr Val Leu
            100                 105                 110

<210> SEQ ID NO 71
<211> LENGTH: 119
<212> TYPE: PRT
<213> ORGANISM: Homo sapiens

<400> SEQUENCE: 71

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Gln Met Val His Gly Leu Asp Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Homo sapiens

<400> SEQUENCE: 72

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Glu Met Gln Asn Gly Gly Leu Asp Tyr Trp Gly Gln Gly
            100                 105                 110

Thr Leu Val Thr Val Ser Ser
        115

<210> SEQ ID NO 73
<211> LENGTH: 119
<212> TYPE: PRT
<213> ORGANISM: Homo sapiens

<400> SEQUENCE: 73
```

-continued

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Glu Met Thr Arg Gly Gly Leu Asp Tyr Trp Gly Gln Gly
                100                 105                 110

Thr Leu Val Thr Val Ser Ser
            115

<210> SEQ ID NO 74
<211> LENGTH: 119
<212> TYPE: PRT
<213> ORGANISM: Homo sapiens

<400> SEQUENCE: 74

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Glu Met His Val Gly Gly Leu Asp Tyr Trp Gly Gln Gly
                100                 105                 110

Thr Leu Val Thr Val Ser Ser
            115

<210> SEQ ID NO 75
<211> LENGTH: 119
<212> TYPE: PRT
<213> ORGANISM: Homo sapiens

<400> SEQUENCE: 75

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

```
Met Glu Leu Thr Arg Leu Thr Ser Asp Asp Thr Ser Val Tyr Tyr Cys
                    85                  90                  95

Ala Arg Asp Glu Met Val Trp Gly Gly Leu Asp Tyr Trp Gly Gln Gly
                100                 105                 110

Thr Leu Val Thr Val Ser Ser
            115

<210> SEQ ID NO 76
<211> LENGTH: 99
<212> TYPE: PRT
<213> ORGANISM: Homo sapiens

<400> SEQUENCE: 76

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 77
<211> LENGTH: 76
<212> TYPE: PRT
<213> ORGANISM: Homo sapiens

<400> SEQUENCE: 77

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr
65                  70                  75

<210> SEQ ID NO 78
<211> LENGTH: 233
<212> TYPE: PRT
<213> ORGANISM: Homo sapiens

<400> SEQUENCE: 78

Val Glu Pro Lys Ser Ser Asp Lys Thr His Thr Ser Pro Pro Ser Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60
```

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 79
<211> LENGTH: 219
<212> TYPE: PRT
<213> ORGANISM: Artificial Sequence
<220> FEATURE:
<223> OTHER INFORMATION: humanized immunoglobulin

<400> SEQUENCE: 79

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 80
<211> LENGTH: 447
<212> TYPE: PRT
<213> ORGANISM: Artificial Sequence
<220> FEATURE:
<223> OTHER INFORMATION: humanized immunoglobulin

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
        35                  40                  45

Ile Gly Tyr Ile Ser Tyr Asp Gly Thr Asn Asn Tyr Lys Pro Ser Leu
    50                  55                  60

Lys Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 81
<211> LENGTH: 118
<212> TYPE: PRT
<213> ORGANISM: Artificial Sequence
<220> FEATURE:
<223> OTHER INFORMATION: immunoglobulin

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser
        115

<210> SEQ ID NO 82
<211> LENGTH: 10
<212> TYPE: PRT
<213> ORGANISM: Artificial Sequence
<220> FEATURE:
<223> OTHER INFORMATION: immunoglobulin

<400> SEQUENCE: 82

Gly Tyr Thr Phe Ser Ser Tyr Gly Met Tyr
1               5                   10

<210> SEQ ID NO 83
<211> LENGTH: 17
<212> TYPE: PRT
<213> ORGANISM: Artificial Sequence
<220> FEATURE:
<223> OTHER INFORMATION: immunoglobulin

<400> SEQUENCE: 83
```

```
Trp Ile Asp Pro Gly Ser Gly Gly Thr Lys Tyr Asn Glu Lys Phe Lys
1               5                   10                  15

Gly
```

<210> SEQ ID NO 84
<211> LENGTH: 9
<212> TYPE: PRT
<213> ORGANISM: Artificial Sequence
<220> FEATURE:
<223> OTHER INFORMATION: immunoglobulin

<400> SEQUENCE: 84

```
Glu Arg Tyr Gly Tyr Tyr Phe Asp Tyr
1               5
```

<210> SEQ ID NO 85
<211> LENGTH: 108
<212> TYPE: PRT
<213> ORGANISM: Artificial Sequence
<220> FEATURE:
<223> OTHER INFORMATION: immunoglobulin

<400> SEQUENCE: 85

```
Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105
```

<210> SEQ ID NO 86
<211> LENGTH: 11
<212> TYPE: PRT
<213> ORGANISM: Artificial Sequence
<220> FEATURE:
<223> OTHER INFORMATION: immunoglobulin

<400> SEQUENCE: 86

```
Arg Ala Ser Gln Tyr Val Gly Ser Tyr Leu Asn
1               5                   10
```

<210> SEQ ID NO 87
<211> LENGTH: 7
<212> TYPE: PRT
<213> ORGANISM: Artificial Sequence
<220> FEATURE:
<223> OTHER INFORMATION: immunoglobulin

<400> SEQUENCE: 87

```
Asp Ala Ser Asn Arg Ala Thr
1               5
```

<210> SEQ ID NO 88
<211> LENGTH: 10
<212> TYPE: PRT

<213> ORGANISM: Artificial Sequence
<220> FEATURE:
<223> OTHER INFORMATION: immunoglobulin

<400> SEQUENCE: 88

Gln Val Trp Asp Ser Ser Pro Pro Val Val
1               5                   10

<210> SEQ ID NO 89
<211> LENGTH: 109
<212> TYPE: PRT
<213> ORGANISM: Artificial Sequence
<220> FEATURE:
<223> OTHER INFORMATION: immunoglobulin

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105

<210> SEQ ID NO 90
<211> LENGTH: 11
<212> TYPE: PRT
<213> ORGANISM: Artificial Sequence
<220> FEATURE:
<223> OTHER INFORMATION: immunoglobulin

<400> SEQUENCE: 90

Arg Ala Ser Gln Asp Val Ser Arg Tyr Leu Thr
1               5                   10

<210> SEQ ID NO 91
<211> LENGTH: 7
<212> TYPE: PRT
<213> ORGANISM: Artificial Sequence
<220> FEATURE:
<223> OTHER INFORMATION: immunoglobulin

<400> SEQUENCE: 91

Ala Ala Ser Ser Leu Gln Ser
1               5

<210> SEQ ID NO 92
<211> LENGTH: 11
<212> TYPE: PRT
<213> ORGANISM: Artificial Sequence
<220> FEATURE:
<223> OTHER INFORMATION: immunoglobulin

<400> SEQUENCE: 92

Gln Ala Tyr Asp Tyr Ser Leu Ser Gly Tyr Val
1               5                   10

```
<210> SEQ ID NO 93
<211> LENGTH: 121
<212> TYPE: PRT
<213> ORGANISM: Artificial Sequence
<220> FEATURE:
<223> OTHER INFORMATION: immunoglobulin

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120

<210> SEQ ID NO 94
<211> LENGTH: 10
<212> TYPE: PRT
<213> ORGANISM: Artificial Sequence
<220> FEATURE:
<223> OTHER INFORMATION: immunoglobulin

<400> SEQUENCE: 94

Gly Tyr Thr Phe Ser Ser Tyr Trp Met His
1               5                   10

<210> SEQ ID NO 95
<211> LENGTH: 17
<212> TYPE: PRT
<213> ORGANISM: Artificial Sequence
<220> FEATURE:
<223> OTHER INFORMATION: immunoblobulin

<400> SEQUENCE: 95

Arg Ile Asp Pro Tyr Asn Gly Gly Thr Lys Tyr Asn Glu Lys Phe Lys
1               5                   10                  15

Gly

<210> SEQ ID NO 96
<211> LENGTH: 12
<212> TYPE: PRT
<213> ORGANISM: Artificial Sequence
<220> FEATURE:
<223> OTHER INFORMATION: immunoglobulin

<400> SEQUENCE: 96

Tyr Gly Tyr Tyr Leu Gly Ser Tyr Ala Met Asp Tyr
1               5                   10

<210> SEQ ID NO 97
<211> LENGTH: 119
<212> TYPE: PRT
```

```
<213> ORGANISM: Artificial Sequence
<220> FEATURE:
<223> OTHER INFORMATION: immunoglobulin

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Asn Gly Gly Ala Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
            100                 105                 110

Thr Leu Val Thr Val Ser Ser
        115

<210> SEQ ID NO 98
<211> LENGTH: 10
<212> TYPE: PRT
<213> ORGANISM: Artificial Sequence
<220> FEATURE:
<223> OTHER INFORMATION: immunoglobulin

<400> SEQUENCE: 98

Gly Tyr Thr Phe Thr Asp Tyr Tyr Met Asn
1               5                   10

<210> SEQ ID NO 99
<211> LENGTH: 17
<212> TYPE: PRT
<213> ORGANISM: Artificial Sequence
<220> FEATURE:
<223> OTHER INFORMATION: immunoglobulin

<400> SEQUENCE: 99

Asp Ile Asn Pro Asn Asn Gly Gly Ala Ile Tyr Asn Gln Lys Phe Lys
1               5                   10                  15

Gly

<210> SEQ ID NO 100
<211> LENGTH: 10
<212> TYPE: PRT
<213> ORGANISM: Artificial Sequence
<220> FEATURE:
<223> OTHER INFORMATION: immunoglobulin

<400> SEQUENCE: 100

Gly Ile Ile Thr Glu Ile Ala Glu Asp Phe
1               5                   10

<210> SEQ ID NO 101
<211> LENGTH: 108
<212> TYPE: PRT
<213> ORGANISM: Artificial Sequence
<220> FEATURE:
<223> OTHER INFORMATION: immunoglobulin
```

```
<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Val Trp Tyr Gln Gln Lys Pro Gly Lys Ala Pro Lys Ala Leu Ile
        35                  40                  45

His Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Gln Tyr Pro Tyr
                85                  90                  95

Thr Phe Gly Gln Gly Thr Lys Val Glu Ile Lys Arg
            100                 105

<210> SEQ ID NO 102
<211> LENGTH: 11
<212> TYPE: PRT
<213> ORGANISM: Artificial Sequence
<220> FEATURE:
<223> OTHER INFORMATION: immunoglobulin

<400> SEQUENCE: 102

Lys Ala Ser Gln Asn Val Gly Thr Ala Val Val
1               5                   10

<210> SEQ ID NO 103
<211> LENGTH: 7
<212> TYPE: PRT
<213> ORGANISM: Artificial Sequence
<220> FEATURE:
<223> OTHER INFORMATION: immunoglobulin

<400> SEQUENCE: 103

Ser Ala Ser Tyr Arg Tyr Ser
1               5

<210> SEQ ID NO 104
<211> LENGTH: 9
<212> TYPE: PRT
<213> ORGANISM: Artificial Sequence
<220> FEATURE:
<223> OTHER INFORMATION: immunoglobulin

<400> SEQUENCE: 104

Gln Gln Tyr Lys Gln Tyr Pro Tyr Thr
1               5
```

CELL LINE 3M

This application claims the benefit of U.S. provisional patent application No. 61/289,703, filed Dec. 23, 2009; which is herein incorporated by reference in its entirety.

FIELD OF THE INVENTION

The field of the invention relates to isolated cells that are useful, e.g., for expression of therapeutic proteins, such as antibodies, as well as to methods of using the cells, for example, to express such proteins.

BACKGROUND OF THE INVENTION

Production of recombinant proteins suitable for use as therapeutics is typically an arduous and costly process. The expression system to be used to express a given protein is partially dependent upon the protein yield derived from each system. In considering a suitable method for antibody manufacture, for example, a variety of factors must be evaluated. These include antibody structure, the importance of carbohydrate, and expression, which includes yield and productivity, ease of purification and cost of goods. The yield greatly affects the cost of goods associated with any such process.

In general, recombinant expression technology in mammalian cell culture has been the principal means for the commercial production of therapeutic antibodies. Mammalian systems are beneficial for antibody production for several reasons including the glycosylation pattern on the expressed product. Often the recombinant proteins are produced in mammalian cell culture using either Chinese hamster ovary (CHO) or mouse myeloma (NS0) cell lines.

Generation of superior cell lines, for recombinant expression, which reach high cell densities and have great longevity in culture produce greater quantities of therapeutic protein per liter of cell culture grown. This leads to a greater efficiency and a lower cost of goods.

SUMMARY OF THE INVENTION

The present invention provides an isolated Chinese hamster ovary (CHO) cell produced by a method comprising: adapting CHO-DXB11 cells into animal-component free medium in suspension, e.g., for about 83 days; then subcloning the cells into said medium, e.g., twice. In an embodiment of the invention, the subcloning steps comprise (a) serially diluting the adapted cells (e.g., by ½ each dilution) in growth medium, for example, in about 100 microliters, e.g., in a microtiter dish comprising, for example, 96 wells; (b) allowing the cells of each dilution to grow; (c) selecting the cells in the highest dilution containing viable cells (e.g., as judged visually, e.g., using a microscope, e.g., to identify the presence of cell colonies); and (d) repeating steps (a), (b) and (c) once more. In an embodiment of the invention, the selected dilution is about 1/64. In an embodiment of the invention, the cell is one that is deposited at the American Type Culture Collection under deposit number PTA-10481. In an embodiment of the invention, the cell is in an aqueous liquid cell culture medium; and/or a vessel such as a vial and/or a freezing medium that contains, e.g., DMSO, e.g., wherein the freezing medium is about 80% serum free medium, about 10% dialyzed fetal bovine serum and about 10% DMSO. Embodiments of the invention include a cell bank or working cell bank comprising the cell. In an embodiment of the invention, the cell comprises a vector which, for example, comprises a polynucleotide encoding one or more proteins such as a light and/or heavy chain immunoglobulin or a fusion protein comprising a polypeptide (e.g., a cytokine or chemokines, e.g., MCP-1) fused to an immunoglobulin (e.g., a Fc) or to human serum albumin. In an embodiment of the invention, the protein encoded by a polynucleotide in the cell is an immunoglobulin comprising an amino acid sequence selected from the group consisting of SEQ ID NOs: 1-8, 21, 22, 42, 43, 58-69, 79, 80, 81, 85, 89, 93 and 101 or a mature fragment thereof or an immunoglobulin comprising one or more CDRs from said immunoglobulin; optionally linked to an immunoglobulin constant chain; or wherein the protein is an immunoglobulin chain comprising:

(1)
CDR-L1:
(SEQ ID NO: 9)
KASKKVTIFGSISALH,

CDR-L2;
NGAKLES (20),
and

CDR-L3:
(SEQ ID NO: 11)
LQNKEVPYT;

(2)
CDR-H1:
(SEQ ID NO: 12)
SYGIT,

CDR-H2:
(SEQ ID NO: 13)
ENYPRSGNTYYNEKFKG,
and

CDR-H3:
(SEQ ID NO: 14)
CEFISTVVAPYYYALDY
or (SEQ ID NO: 15)
SEFISTVVAPYYYALDY
or (SEQ ID NO: 16)
AEFISTVVAPYYYALDY
or (SEQ ID NO: 17)
VEFISTVVAPYYYALDY
or (SEQ ID NO: 18)
SEFISTVMAPYYYALDY
or (SEQ ID NO: 19)
SEFTSTVVAPYYYALDY;

(3)
CDRH1:
(SEQ ID NO: 23)
Gly Phe Thr Phe Ser Ser Tyr Thr Met Ser,

CDRH2:
(SEQ ID NO: 24)
Thr Ile Ser Ser Gly Gly Thr Tyr Thr Tyr Tyr Pro
Asp Ser Val Lys Gly,
and CDRH3:
(SEQ ID NO: 25)
Asp Asn His Ala Tyr Asp Arg Gly Pro Phe Phe Asp
Tyr;

(4)
CDRL1:
(SEQ ID NO: 26)
Lys Ser Ser Gln Asn Leu Phe Tyr Arg Ser Asn Gln
Lys Asn His Leu Ala,

CDRL2:
(SEQ ID NO: 27)
Trp Thr Ser Thr Arg Glu Ser,
and

CDRL3:
(SEQ ID NO: 28)
Gln Gln Tyr Tyr Ser Tyr Pro Pro Thr;

(5)
CDRH1:
(SEQ ID NO: 29)
Ala Tyr Gly Met Asp,

CDRH2:
(SEQ ID NO: 30)
Ser Ile Ser Pro Ser Gly Gly Arg Thr Lys Tyr Ala
Asp Ser Val Lys Gly,
and CDRH3:
(SEQ ID NO: 31)
Asp Leu Gly Gly Gly Tyr Tyr Tyr Tyr Gly Met
Asp Val;

(6)
CDRL1:
(SEQ ID NO: 32)
Thr Gly Thr Ser Ser Asp Val Gly Gly Tyr Asn Tyr
Val Ser,

CDRL2:
(SEQ ID NO: 33)
Glu Val Ser Asn Arg Pro Ser,
and

CDRL3:
(SEQ ID NO: 34)
Ser Ser Tyr Thr Ser Ser Ser Thr Leu Phe Tyr Val;

(7)
CDRH1:
(SEQ ID NO: 35)
GKTFWSWGIN,

CDRH2:
(SEQ ID NO: 36)
YIYIGTGYTEPNPKYKG,
and

CDRH3:
(SEQ ID NO: 37)
IGGYYGNFAD
or
(SEQ ID NO: 38)
IGGYYGNF<u>DQ</u>;

(8)
CDRL1:
(SEQ ID NO: 39)
RSSQSLLISGGNTYLN,

CDRL2:
(SEQ ID NO: 40)
LVSKLDQ,
and

CDRL3:
(SEQ ID NO: 41)
WQGTYFPLT;

(9)
CDRH1:
(SEQ ID NO: 44)
TYWMH
or
(SEQ ID NO: 45)
TYWMH,

CDRH2:
(SEQ ID NO: 46)
EINPTNGHTNYNEKFKS,
(SEQ ID NO: 47)
EINPTNGHTNYNPSFQG,
or
(SEQ ID NO: 48)
EINPTNGHTNYNQKFQG,
and CDRH3:
(SEQ ID NO: 49)
NYVGSIFDY
or
(SEQ ID NO: 50)
NYVGSIFDY;

(10)
CDRL1:
(SEQ ID NO: 51)
KASENVVSYVS
or
(SEQ ID NO: 52)
KASENVVSYVS,

CDRL2:
(SEQ ID NO: 53)
GASNRNT,
(SEQ ID NO: 54)
GASNRNT
or
(SEQ ID NO: 55)
GASNRES,
and CDRL3:
(SEQ ID NO: 56)
GQSYNYPYT
or
(SEQ ID NO: 57)
GQSYNYPYT;

optionally linked to an immunoglobulin constant chain.

The present invention also provides a method for making said cell comprising adapting CHO-DXB11 cells into animal-component free medium in suspension for 83 days; then subcloning the cells into said medium twice.

The present invention also provides a method for making one or more polypeptides (e.g., an immunoglobulin) comprising introducing one or more polynucleotides encoding said polypeptides into the cell and culturing the cell line in conditions under which the polypeptides are produced; and, optionally, isolating the polypeptide. In an embodiment of the invention, the immunoglobulin an amino acid sequence selected from the group consisting of SEQ ID NOs: 1-8, 21, 22, 42, 43, 58-69, 79, 80, 81, 85, 89, 93 and 101 or a mature fragment thereof or an immunoglobulin comprising one or more CDRs from said immunoglobulin; optionally linked to an immunoglobulin constant chain. In an embodiment of the invention, the immunoglobulin comprises:

(1)
CDR-L1:
 (SEQ ID NO: 9)
KASKKVTIFGSISALH,

CDR-L2:
 (SEQ ID NO: 10)
NGAKLES,
and

CDR-L3:
 (SEQ ID NO: 11)
LQNKEVPYT;

(2)
CDR-H1:
 (SEQ ID NO: 12)
SYGIT,

CDR-H2:
 (SEQ ID NO: 13)
ENYPRSGNTYYNEKFKG,
and

CDR-H3:
 (SEQ ID NO: 14)
CEFISTVVAPYYYALDY
or
 (SEQ ID NO: 15)
SEFISTVVAPYYYALDY
or
 (SEQ ID NO: 16)
AEFISTVVAPYYYALDY
or
 (SEQ ID NO: 17)
VEFISTVVAPYYYALDY
or
 (SEQ ID NO: 18)
SEFISTVMAPYYYALDY
or
 (SEQ ID NO: 19)
SEFTSTVVAPYYYALDY;

(3)
CDRH1:
 (SEQ ID NO: 23)
Gly Phe Thr Phe Ser Ser Tyr Thr Met Ser,

CDRH2:
 (SEQ ID NO: 24)
Thr Ile Ser Ser Gly Gly Thr Tyr Thr Tyr Tyr Pro
Asp Ser Val Lys Gly,
and CDRH3:
 (SEQ ID NO: 25)
Asp Asn His Ala Tyr Asp Arg Gly Pro Phe Phe Asp
Tyr;

(4)
CDRL1:
 (SEQ ID NO: 26)
Lys Ser Ser Gln Asn Leu Phe Tyr Arg Ser Asn Gln
Lys Asn His Leu Ala,

CDRL2:
 (SEQ ID NO: 27)
Trp Thr Ser Thr Arg Glu Ser,
and

CDRL3:
 (SEQ ID NO: 28)
Gln Gln Tyr Tyr Ser Tyr Pro Pro Thr;

(5)
CDRH1:
 (SEQ ID NO: 29)
Ala Tyr Gly Met Asp,

CDRH2:
 (SEQ ID NO: 30)
Ser Ile Ser Pro Ser Gly Gly Arg Thr Lys Tyr Ala
Asp Ser Val Lys Gly,
and CDRH3:
 (SEQ ID NO: 31)
Asp Leu Gly Gly Gly Tyr Tyr Tyr Tyr Gly Met
Asp Val;

(6)
CDRL1:
 (SEQ ID NO: 32)
Thr Gly Thr Ser Ser Asp Val Gly Gly Tyr Asn Tyr
Val Ser,

CDRL2:
 (SEQ ID NO: 33)
Glu Val Ser Asn Arg Pro Ser,
and

CDRL3:
 (SEQ ID NO: 34)
Ser Ser Tyr Thr Ser Ser Ser Thr Leu Phe Tyr Val;

(7)
CDRH1:
 (SEQ ID NO: 35)
GKTFWSWGIN,

CDRH2:
 (SEQ ID NO: 36)
YIYIGTGYTEPNPKYKG,
and

CDRH3:
 (SEQ ID NO: 37)
IGGYYGNFAD
or
 (SEQ ID NO: 38)
IGGYYGNF<u>DQ</u>;

(8)
CDRL1:
 (SEQ ID NO: 39)
RSSQSLLISGGNTYLN,

CDRL2:
 (SEQ ID NO: 40)
LVSKLDQ,
and

CDRL3:
 (SEQ ID NO: 41)
WQGTYFPLT;

(9)
CDRH1:
 (SEQ ID NO: 44)
TYWMH
or
 (SEQ ID NO: 45)
TYWMH,

CDRH2:
 (SEQ ID NO: 46)
EINPTNGHTNYNEKFKS, (SEQ ID NO: 47)

```
EINPTNGHTNYNPSFQG,
or
                                    (SEQ ID NO: 48)
EINPTNGHTNYNQKFQG,
and CDRH3:
                                    (SEQ ID NO: 49)
NYVGSIFDY
or
                                    (SEQ ID NO: 50)
NYVGSIFDY;
or

(10)
CDRL1:
                                    (SEQ ID NO: 51)
KASENVVSYVS
or
                                    (SEQ ID NO: 52)
KASENVVSYVS,

CDRL2:
                                    (SEQ ID NO: 53)
GASNRNT,
                                    (SEQ ID NO: 54)
GASNRNT
or
                                    (SEQ ID NO: 55)
GASNRES,
and CDRL3:
                                    (SEQ ID NO: 56)
GQSYNYPYT
or
                                    (SEQ ID NO: 57)
GQSYNYPYT;
``` optionally linked to an immunoglobulin constant chain. In an embodiment of the invention, the immunoglobulin is a light chain immunoglobulin linked to a kappa or lambda constant immunoglobulin chain and/or wherein the immunoglobulin is a heavy chain immunoglobulin linked to a gamma-1, gamma-2, gamma-3 or gamma-4 constant immunoglobulin chain.

The present invention also provides a method for producing an antibody comprising inoculating an initial mammalian cell growth medium, pre-warmed to about 37° C.; which initial medium comprises HEPES, sodium bicarbonate buffers, inorganic salts, non-essential amino acids, recombinant human insulin, trace elements and surfactants; and which does not comprise L-glutamine, antibiotics, antimycotics or animal-derived components; with one or more of said cells expressing the antibody light chain immunoglobulin and heavy chain immunoglobulin, to a cell density of about 2.5-$5 \times 10^5$ cells/ml; and, adding the following supplements to the medium before, simultaneously with or immediately after said inoculation:
soy hydrolysate to a final concentration of about 10 g/liter; and, optionally, an amino acid feed wherein the concentration of the components added by said amino acid feed are approximately those set forth below:

| | |
|---|---|
| L-arginine: | 126.4 mg/liter |
| L-cystine: | 34 mg/liter |
| L-histidine: | 42 mg/liter |
| L-isoleucine: | 52 mg/liter |
| L-leucine: | 52 mg/liter |
| L-lysine: | 72 mg/liter |
| L-Methionine: | 15.2 mg/liter |
| L-phenylalanine: | 33 mg/liter |
| L-threonine: | 47.6 mg/liter |
| L-tryptophan: | 10.2 mg/liter |
| L-tyrosine: | 36 mg/liter |
| L-valine: | 46.8 mg/liter |
| L-alanine: | 8.9 mg/liter |
| L-asparagine: | 30 mg/liter |
| L-aspartic acid: | 26.6 mg/liter |
| L-glutamic acid: | 29.4 mg/liter |
| glycine: | 15 mg/liter |
| L-proline: | 23 mg/liter |
| L-serine: | 21 mg/liter; | and, when viable cell density reaches over about $1.2 \times 10^6$ cells/ml, adding supplement feeds wherein the concentration of the components added by said supplement feeds are approximately those set forth below:

| | |
|---|---|
| Sodium selenite: | 0.01426 mg/liter |
| Adenine sulfate: | 1.632 mg/liter |
| Adenosine: | 17.6 mg/liter |
| Cytidine: | 17.6 mg/liter |
| Guanosine: | 17.6 mg/liter |
| Uridine: | 17.6 mg/liter |
| Hypoxanthine: | 11.8 mg/liter |
| L-citrulline: | 12.6 mg/liter |
| L-ornithine-HCl: | 25.6 mg/liter |
| Biotin: | 0.28 mg/liter |
| Flavin Adenine Dinucleotide: | 0.05 mg/liter |
| Folic Acid: | 4.6 mg/liter |
| Lipoic Acid: | 0.52 mg/liter |
| Niacin: | 31.4 mg/liter |
| Pyridoxine HCl: | 3 mg/liter |
| Riboflavin: | 1.86 mg/liter |
| Thiamine HCl: | 16 mg/liter |
| Vitamin E: | 0.376 mg/liter |
| Vitamin B12: | 3.4 mg/liter |
| Choline Chloride: | 50.2 mg/liter |
| Ethanolamine HCl: | 4.4 mg/liter |
| i-Inositol: | 73.2 mg/liter |
| Thymidine: | 7.8 mg/liter |
| Putrescine 2HCl: | 0.4 mg/liter |
| Progesterone: | 0.015 mg/liter |
| D-Calcium Pantothenate: | 23.8 mg/liter |
| L-asparagine: | 812 mg/liter |
| L-proline: | 216 mg/liter |
| L-isoleucine | 370 mg/liter |
| L-cysteine-HCl | 224 mg/liter |
| L-leucine | 332 mg/liter |
| L-threonine | 164 mg/liter |
| L-tyrosine | 198 mg/liter |
| L-arginine | 186 mg/liter |
| L-aspartic acid | 71 mg/liter |
| L-glutamic acid | 126 mg/liter |
| Glycine | 57 mg/liter |
| L-histidine | 125 mg/liter |
| L-methionine | 132 mg/liter |
| L-tryptophan | 99 mg/liter |
| L-lysine | 293 mg/liter |
| L-phenylalanine | 174 mg/liter |
| L-valine | 262 mg/liter |
| L-serine: | 260 mg/liter |
| Sodium phosphate monobasic: | 288.2 mg/liter |
| Zinc sulfate: | 1.08 mg/liter |
| Cupric sulfate: | 0.0032 mg/liter |
| Ammonium vanadate: | 0.00078 mg/liter |
| Cobalt chloride: | 0.0025 mg/liter |
| Nickel dichloride hexahydrate: | 0.0004 mg/liter |
| Sodium molybdate dehydrate: | 0.00016 mg/liter; | and, maintaining glucose concentration in the medium at about 1.5 g/liter and maintaining L-glutamine concentration in the medium at about 150 mg/liter; and during cell growth maintaining $O_2$ concentration at about 60%; pH at about 6.8±0.02 and temperature at about 36.5° C.±0.5° C.; and, optionally, removing the host cells from the medium when cell viability is below about 60%; and, optionally, recovering the culture medium from the cells by disk-stack centrifuging the medium, depth filtering the medium and filtering the medium through a filter with about a 0.2 micron pore size; and/or, optionally, purifying the immunoglobulins from the medium by column chromatographic fractionation.

DETAILED DESCRIPTION OF THE INVENTION

Figure 1:
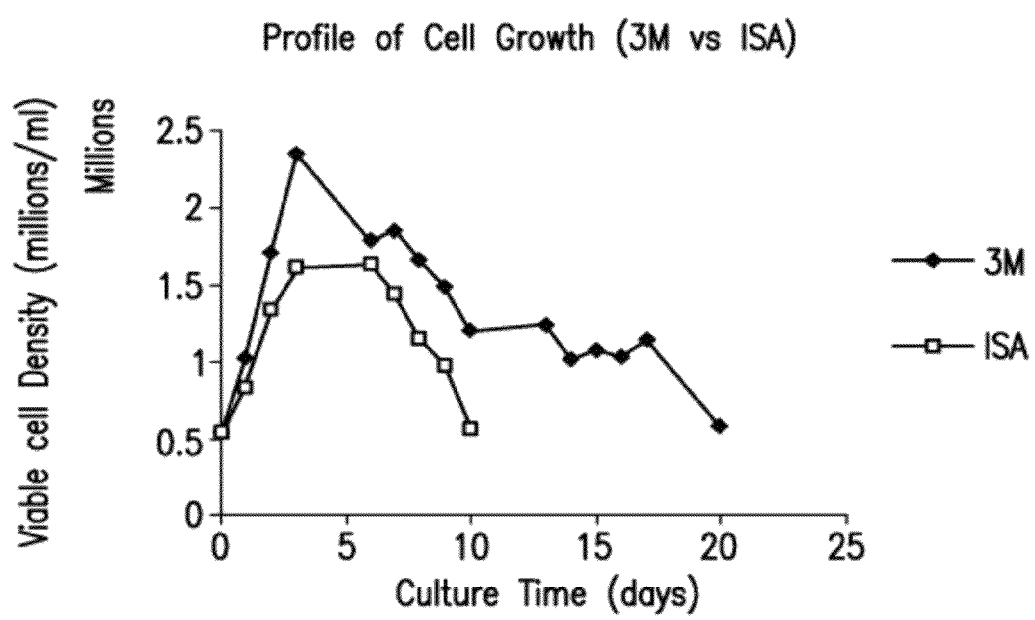
FIG. 1. Evaluation of Cell Growth Potential for 3M and ISA Host Cells in batch mode.

The present invention provides an isolated Chinese Hamster Ovary (CHO-DXB11) cell for therapeutic antibody production, 3M. 3M cells were deposited, under the Budapest Treaty, on Nov. 17, 2009 with the American Type Culture Collection (ATCC); 10801 University Boulevard; Manassas, Va. 20110-2209. The cells were deposited at the ATCC under deposit number PTA-10481. All restrictions on access to the cells deposited in ATCC will be irrevocably removed upon grant of a patent.

The present invention also includes derivatives of the cell lines of the present invention. Derivatives include mutants comprising the 3M genetic background for the for the presence of one or more additional genetic mutations, e.g., wherein such derivative cell lines retain the beneficial properties of the parental 3M cell line (e.g., protein production in serum free suspension culture, cell growth and/or clone recovery rate).

The 3M cell line originated from the well known Chinese Hamster Ovary cell line, CHO-DXB11. CHO DXB11 cells are available from the American Type Culture Collection, e.g., under deposit no. CRL-11397. Briefly, CHO-DXB11 was suspension-adapted for three months followed by two rounds of subsequent cloning in a serum-free protein-free medium. Relative to previously developed and known cell lines, the 3M cell line is robust in cell growth, superior in clone recovery efficiency and produces high antibody titers in suspension mode in serum-free media. 3M has been used to generate highly productive clones for production of several antibodies.

The present invention includes not only individual isolated 3M cells but also master cell banks (MCB) and working cell banks (WCB), e.g., comprising 3M cells that comprise one or more genes encoding therapeutic proteins to be expressed. Typically, when a cell line is to be used over many manufacturing cycles, a two-tiered cell banking system consisting of a master cell bank or master seed bank and a working cell bank can be established. A cell line is generally established from a single host cell clone and this cell line is used to make-up the MCB. Generally, this MCB must be characterized and extensively tested for contaminants such as bacteria, fungi, viruses and mycoplasma. A sample of cells from the MCB can be expanded to form the WCB, which is characterized for cell viability prior to use in a manufacturing process. The cells in a MCB or WCB can be stored in vials, for example, at low temperature (e.g., 0° C. or lower, −20° C. or −80° C., or in liquid nitrogen, e.g., at −110° C. to −180° C.). Typically, the working cell bank includes cells from one vial of the master bank which have been grown for several passages before storage. In general, when future cells are needed, they are taken from the working cell bank; whereas, the master cell bank is used only when necessary, ensuring a stock of cells with a low passage number to avoid genetic variation within the cell culture.

Subcloning refers to a progressive dilution of cells in series, e.g., in wells of a 96 well microliter plate, in predetermined ratios to produce single colonies.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (DN. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, at al. (eds.), *Current Protocols in Molecular Biology*, John Wiley & Sons, Inc. (1994).

A "polynucleotide", "nucleic acid" or "nucleic acid molecule" DNA and RNA (e.g., mRNA), single or double stranded.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids.

The terms "isolated polynucleotide" or "isolated polypeptide" include a polynucleotide (e.g., RNA or DNA molecule, or a mixed polymer) or a polypeptide, respectively, which are partially (to any degree) or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, in an embodiment of the invention, be an essentially homogeneous composition.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism (e.g., a CHO cell such as 3M) that is selected, modified, transfected, transformed, grown, or used or manipulated in any way, for the production of a substance by the cell, for example the expression or replication, by the cell, of a gene, a DNA or RNA sequence or a protein. Host cells also include bacterial cells (e.g., E. coli), murine macrophage J774 cells or any other macrophage cell line and human intestinal epithelial Caco2 cells.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, at al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., Cloning Vectors: A Laboratory Manual, 1985 and Supplements, Elsevier, N.Y., and Rodriguez et al., (eds.), Vectors: A Survey of Molecular Cloning Vectors and Their Uses, 1988, Buttersworth, Boston, Mass.

The term "expression system" means a host cell (e.g., a 3M cell) and compatible vector which, under suitable conditions, can express a protein or nucleic acid which is carried by the vector and introduced to the host cell.

Mutant CHO cells comprising the 3M cell genetic background are also within the scope of the present invention. Such mutant cells are identical to a 3M cell of the present invention but for the presence of one or more additional genetic mutations. Genetic mutations can take the form of gene knock-outs, deletions, point mutations, etc. Accordingly, the present invention includes methods for generating a 3M cell line mutant comprising adapting CHO-DXB11 cells into animal-component free medium in suspension for 83 days; then subcloning the cells into said medium twice, then introducing one or more genetic mutations into such cells. Cells produced by such a method are also within the scope of the present invention. Methods for introducing genetic mutations into CHO cells are within the ability of any practitioner of ordinary skill in the art. For example, mutations may be introduced by way of chemical or radiation mutagenesis (e.g., using ethyl methanesulfonate (EMS) treatment, N-methyl-N-nitro-N-nitrosoguanidine (NG) treatment, ultraviolet (UV) light treatment, gamma irradiation, X-ray irradiation, fast neutron irradiation) or homologous recombination based methods for introducing mutations (e.g., site-directed mutagenesis, for example PCR-based introduction of a specific point mutation or recombinant knock out or knock-in of a given gene or locus). Chromosomal locations into which mutations may be introduced may be selected from those appearing in the public sequence databases.

3M Cells

The present invention includes an isolated Chinese hamster ovary cell, the "3M" cell, the exhibits superior properties allowing efficient production of various polypeptides. An embodiment of the 3M cells of the present invention were deposited, under the Budapest Treaty, on Nov. 17, 2009 with the American Type Culture Collection (ATCC); 10801 University Boulevard; Manassas, Va. 20110-2209. The cells were deposited at the ATCC under deposit number PTA-10481. All restrictions on access to the cells deposited in ATCC will be irrevocably removed upon grant of a patent. 3M cells may be produced by method comprising adapting CHO-DXB11 cells into animal-component free medium in suspension for about 3 months (e.g., about 83 days or about 80-90 days or about 90 days); then subcloning the cells into said medium twice.

Subcloning can be performed by a method comprising the steps of
(a) serially diluting the adapted cells in serum-free growth medium (e.g., any of those discussed herein), for example, animal component-free medium;
e.g., wherein the cells are diluted by ½ each time.
e.g., wherein the serial dilutions are done in a low volume of about 100 microliters.
e.g., wherein the serial dilutions are done in the wells of a 96 well microtiter plate.
(b) allowing the cells of each dilution to grow;
e.g., wherein the cells are allowed to grow for about 2 weeks
e.g., wherein the cells are allowed to grow in high humidity and/or 7.5% $CO_2$.
e.g., wherein the cells are allowed to grow at 37° C.
(c) selecting the cells in the highest dilution (i.e., lowest concentration of cells) containing viable cells;
e.g., wherein the cells in a dilution are determined to be viable upon visual inspection e.g., using a microscope wherein cellular colonies are observed.
e.g., wherein the highest dilution is about 1/64.
e.g., wherein cells that are selected are transferred into a higher volume (e.g., about 2 ml of medium, e.g., in a T-25 flask) of serum free growth medium and allowed to grow (e.g., shaking at about 70 rpm e.g., for about 1 week, e.g., at about 37° C., e.g., at about 7.5% $CO_2$) before proceeding to step (d) and then re-serially diluting the cells.
and
(d) repeating steps (a), (b) and (c) once more.

Proteins

The present invention includes embodiments comprising methods for recombinantly producing proteins, such as immunoglobulin chains or therapeutic proteins, in the 3M cells. Such immunoglobulin chains include the light and/or heavy immunoglobulin chains for the following antibodies: anti-IL23 (e.g., anti-p19), anti-PD1, anti-TSLP, anti-HGF, anti-IL17, anti-IL23 Receptor, anti-BTLA, cyno-anti-TSLP (cynomolgus frameworks and Ig constant domain, specific for cynomologous monkey TSLP) as well as sB4-HSA (HAS is human serum albumin), mouse Embrel (soluble mouse TNF receptor linked to a mouse Fc portion of an IgG1), and cTLA4-IgG. Such methods are discussed in detail herein. In an embodiment of the invention, the immunoglobulin forms part of an antibody (e.g., human antibody, humanized antibody, chimeric antibody) or antigen-binding fragment thereof, e.g., including an immunoglobulin light and/or heavy chain variable region, optionally linked with an immunoglobulin constant region.

For example, the present invention includes methods wherein a protein to be expressed in a 3M cell (e.g., a light chain and/or heavy chain immunoglobulin) is encoded by a polynucleotide in a plasmid vector, e.g., wherein the polynucleotide is operably linked to a promoter such as a CMV promoter. In an embodiment of the invention, the light and heavy chains are included in a single plasmid vector or in two separate plasmid vectors.

In an embodiment of the invention, the immunoglobulin chain encodes any of those set forth below; for example, any of the following immunoglobulin light and/or heavy chains and/or any of the CDRs thereof (e.g., all 3 from a single light or heavy chain). Dotted, underscored type encodes the signal peptide. Solid underscored type encodes the CDRs. Plain type encodes the framework regions. In an embodiment of the invention, the chains are expressed with the signal peptide which is cleaved upon secretion from the host cell to generate a mature fragment of the chain.

The present invention also comprises compositions including 3M cells in the presence of heavy and/or light immunoglobulin chains and/or antibodies comprising the chain(s) or antigen-binding fragments thereof, e.g., which are in a liquid cell growth culture medium, e.g., wherein such chains were secreted from a host cell (e.g., 3M).

Processes for producing any of the following immunoglobulin polypeptide chains comprising any of the following amino acid sequences or mature fragments thereof or antibodies or antigen-binding fragments thereof comprising such chains or fragments in 3M cells form part of the present invention along with 3M cells themselves comprising the polypeptides and/or polynucleotides encoding said polypeptides (e.g., in a vector). In an embodiment of the invention, the protein is a light or heavy chain immunoglobulin variable chain (either mature (lacking the secretion signal) or unprocessed), optionally linked to an immunoglobulin heavy or light constant chain immunoglobulin, e.g., wherein the variable region comprises an amino acid sequence set forth below, or a mature fragment thereof or wherein the immunoglobulin comprises one or more CDRs (e.g., 3 light chain CDRs or 3 heavy chain CDRs) from those set forth herein:

```
19D12/15H12 Light Chain
                                                (SEQ ID NO: 1)
MSPSQLIGFLLLWVPASRGEIVLTQVPDFQSVTPKEKVTITCRASQSIGSSLHWYQQKPD

QSPKLLIKYASQSLSGVPSRFSGSGSGTDFTLTINSLEAEDAAAYYCHQSSRLPHTFGGG

TKVEIKRT

19D12/15H12 Heavy Chain
                                                (SEQ ID NO: 2)
MEFGLSWVFLVAILKGVQCEVQLVQSGGGLVHPGGSLRLSCAASGFTFSSFAMHWVRQAP

GKGLEWISVIDTRGATYYADSVKGRFTISRDNAKNSLYLQMNSLRAEDMAVYYCARLGNF
```

YYGMDVWGQGTTVTVSS

19D12/15H12 Light Chain-C (LCC) (SEQ ID NO: 3)

M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D A

A A Y Y C H Q S S R L P H T F G Q

G T K V E I K R T

19D12/15H12 Light Chain-D (LCD) (SEQ ID NO: 4)

M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D F

A V Y Y C H Q S S R L P H T F G Q

G T K V E I K R T

19D12/15H12 Light Chain-E (LCE) (SEQ ID NO: 5)

M S P S Q L I G F L L L W V P A S

R G E I V L T Q S P G T L S V S P

G E R A T L S C R A S Q S I G S S

L H W Y Q Q K P G Q A P R L L I K

Y A S Q S L S G I P D R F S G S G

S G T D F T L T I S R L E P E D A

A A Y Y C H Q S S R L P H T F G Q

G T K V E I K R T

19D12/15H12 Light Chain-F (LCF) (SEQ ID NO: 6)

M S P S Q L I G F L L L W V P A S

R G E I V L T Q S P G T L S V S P

G E R A T L S C R A S Q S I G S S

L H W Y Q Q K P G Q A P R L L I K

Y A S Q S L S G I P D R F S G S G

```
-continued
S G T D F T L T I S R L E P E D F

A V Y Y C H Q S S R L P H T F G Q

G T K V E I K R T

19D12/15H12 heavy chain-A (HCA)
                                                                    (SEQ ID NO: 7)
Met Glu Phe Gly Leu Ser Trp Val Phe Leu Val Ala Ile Leu Lys Gly Val Gln Cys Glu Val Gln Leu Val Gln Ser Gly Gly Gly Leu Val Lys Pro Gly Gly Ser Leu Arg Leu Ser Cys Ala Ala Ser Gly Phe Thr Phe Ser Ser Phe Ala Met His Trp Val Arg Gln Ala Pro Gly Lys Gly Leu Glu Trp Ile Ser Val Ile Asp Thr Arg Gly Ala Thr Tyr Tyr Ala Asp Ser Val Lys Gly Arg Phe Thr Ile Ser Arg Asp Asn Ala Lys Asn Ser Leu Tyr Leu Gln Met Asn Ser Leu Arg Ala Glu Asp Thr Ala Val Tyr Tyr Cys Ala Arg Leu Gly Asn Phe Tyr Tyr Gly Met Asp Val Trp Gly Gln Gly Thr Thr Val Thr Val Ser Ser 19D12/15H12 heavy chain-B (HCB)
                                                                    (SEQ ID NO: 8)
Met Glu Phe Gly Leu Ser Trp Val Phe Leu Val Ala Ile Leu Lys Gly Val Gln Cys Glu Val Gln Leu Val Gln Ser Gly Gly Gly Leu Val Lys Pro Gly Gly Ser Leu Arg Leu Ser Cys Ala Ala Ser Gly Phe Thr Phe Ser Ser Phe Ala Met His Trp Val Arg Gln Ala Pro Gly Lys Gly Leu Glu Trp Ile Ser Val Ile Asp Thr Arg Gly Ala Thr Tyr Tyr Ala Asp Ser Val Lys Gly Arg Phe Thr Ile Ser Arg Asp Asn Ala Lys Asn Ser Leu Tyr Leu Gln Met Asn Ser Leu Arg Ala Glu Asp Thr Ala Val Tyr Tyr Cys Ala Arg Leu Gly Asn Phe Tyr Tyr Gly Met Asp Val Trp Gly Gln Gly Thr Thr Val Thr Val Ser Ser
```

See international application publication no. WO2003/100008 which is incorporated herein by reference in its entirety.

Other variable heavy and light chain immunoglobulins that can form part of an anti-IGF1R antibody and antigen-binding fragment thereof are as follows:

```
V_H domains
(1) EVQLVQSGGGLVHPGGSLRLSCAGS  GFTERNYAMY  WVRQAPGKGLEWVS  AIG-SGGGTYYADSVKG (2) QVELVESGGGVVQPGRSQRLSCAAS  GFTFSSYGMH  WVRQAPGKGLEWVA  IIWFDGSSTYYADSVRG (3) EVQLLESGGGLVQPGGSLRLSCTAS  GFTFSSYAMN  WVRQAPGKGLEWVS  AISGSGGTTFYADSVKG (4) EVQLVQSGAEVKKPGSSVKVSCKAS  GGTFSSYAIS  WVRQAPGQGLEWMG  GIIPIFGTANYAQKFQG (5) QVQLQESGPGLVKPSGTLSLTCAVS  GGSISSSNWWS  WVRQPPGKGLEWIG  EIY-HSGSTNYNPSLKS (6) QVQLQESGPGLVKPSETLSLTCTVS  GYSISGGYLWN  WIRQPPGKGLEWIG  YIS-YDGTNNYKPSLKD (1) RFTISRDNAKNSLYLQMNSLRAEDMAVYYCAR  APNWGSDA----------FDI  WGQGTMVTVSS (2) RFTISRDNSKNTLYLQMNSLRAEDTAVYFCAR  ELGRR------------YFDL  WGRGTLVSVSS (3) RFTISRDNSRTTLYLQMNSLRAEDTAVYYCAK  DLGWSDS-----YYYYYGMDV  WGQGTTVTVSS
```

```
-continued
(4) RVTITADKSTSTAYMELSSLRSEDTAVYYCAR APLRFLEWSTQDHYYTYYMDV WGKGTTVTVSS (5) RVTISVDKSKNQFSLKLSSVTAADTAVYYCAR WTGRTD----------AFDI WGQGTWVTVSS (6) RVTISVDTSKNQFSLKLSSVTAADTAVYYCAR YGRV------------FFDY WGQGTLVTVSS 1 = SEQ ID NO: 58
2 = SEQ ID NO: 60
3 = SEQ ID NO: 62
4 = SEQ ID NO: 64
5 = SEQ ID NO: 66
6 = SEQ ID NO: 68

V_L Domains
(a) DIQMTQSPSSLSASVGDRVTITC  RASQGISSWLA       WYQQKPEKAPKSLIY AASSLQS (b) EIVLTQSPATLSLSPGERATLSC  RASQSVSSYLA       WYQQKPGQAPRLLIY DASKRAT (c) DIQMTQFPSSLSASVGDRVTITC  RASQGIRNDLG       WYQQKPGKAPKRLIY AASRLHR (d) SSELTQDP-AVSVALGQTVRITC  QGDSLRSYYAT       WYQQKPGQAPILVIY GENKRPS (e) DVVMTQSPLSLPVTPGEPASISC  RSSQSLLHSNGYNYLD  WYLQKPGQSPQLLIY LGSNRAS (f) DIVMTQSPLSLPVTPGEPASISC  RSSQSIVHSNONTYLQ  WYLQKPGQSPQLLIY KVSNRLY (a) GVPSRFSGSGSGTDFTLTISSLQPEDFATYYC  QQYNSYPPT     FGPGTKVDIK (b) GIPARFSGSGSGTDFTLTISSLEPEDFAVYYC  QQRSKWPPWT    FGQGTKVESK (c) GVPSRFSGSGSGTEFTLTISSLQPEDFATYYC  LQHNSYPCS     FGQGTKLEIKRT (d) GIPDRFSGSSSGNTASLTITGAQAEDEADYYC  KSRDGSGQHLV   FGGGTKLTVLG (e) GVPDRFSGSGSGTDFTLKISRVEAEDVGVYYC  MQGTHWPLT     FGQGTKVEIK (f) GVPDRFSGSGSGTDFTLKISRVEAEDVGVYYC  FQGSMVPWT     FGQGTKVEIK a = SEQ ID NO: 59
b = SEQ ID NO: 61
c = SEQ ID NO: 63
d = SEQ ID NO: 65
e = SEQ ID NO: 67
f = SEQ ID NO: 69
```

In an embodiment of the invention, $V_H1$ is paired, in an antibody or antigen-binding fragment thereof, with $V_La$; $V_H2$ is paired, in an antibody or antigen-binding fragment thereof, with $V_Lb$; $V_H3$ is paired, in an antibody or antigen-binding fragment thereof, with $V_Lc$; $V_H4$ is paired, in an antibody or antigen-binding fragment thereof, with $V_Ld$; $V_H5$ is paired, in an antibody or antigen-binding fragment thereof, with $V_Le$; and/or $V_H6$ is paired, in an antibody or antigen-binding fragment thereof, with $V_Lf$.

Embodiments of the invention include those wherein the immunoglobulin is expressed in 3M cells, for example, in combination of any of those set forth herein (e.g., LCC and HCA; or LCF and HCA; or LCC and HCB). Pairing of the light and heavy chains can result in generation of an antibody or antigen-binding fragment thereof.

In an embodiment of the invention, the polypeptide is one or more immunoglobulin chains that can form an anti-IGF1R antibody or antigen-binding fragment thereof that comprises the light and/or heavy chain immunoglobulins set forth below, or variable regions thereof, or chains that comprise the 3 light chain CDRs and/or 3 heavy chain CDRs that, in an embodiment of the invention, are underscored in the sequences set forth below, e.g., wherein the antibody or fragment comprises the two light and two heavy chain immunoglobulins set forth below:

```
LIGHT CHAIN (1)
                                                        (SEQ ID NO: 79)
  1 DIVMTQSPLS LPVTPGEPAS ISCRSSQSIV HSNGNTYLQW YLQKPGQSPQ

51 LLIYKVSNRL YGVPDRFSGS GSGTDFTLKI SRVEAEDVGV YYCFQGSHVP

101 WTFGQGTKVE IKRTVAAPSV FIFPPSDEQL KSGTASVVCL LNNFYPREAK

151 VQWKVDNALQ SGNSQESVTE QDSKDSTYSL SSTLTLSKAD YEKHKVYACE

201 VTHQGLSSPV TKSFNRGEC

HEAVY CHAIN (2)
                                                        (SEQ ID NO: 80)
  1 QVQLQESGPG LVKPSETLSL TCTVSGYSIT GGYLWNWIRQ PPGKGLEWIG

51 YISYDGTNNY KPSLKDRVTI SRDTSKNQFS LKLSSVTAAD TAVYYCARYG
```

-continued

```
101 RVFFDYWGQG TLVTVSSAST KGPSVFPLAP SSKSTSGGTA ALGCLVKDYF

151 PEPVTVSWNS GALTSGVHTF PAVLQSSGLY SLSSVVTVPS SSLGTQTYIC

201 NVNHKPSNTK VDKRVEPKSC DKTHTCPPCP APELLGGPSV FLEPPKPKDT

251 LMISRTPEVT CVVVDVSHED PEVKFNWYVD GVEVHNAKTK PREEQYNSTY

301 RVVSVLTVLH QDWLNGKEYK CKVSNKALPA PIEKTISKAK GQPREPQVYT

351 LPPSREEMTK NQVSLTCLVK GFYPSDIAVE WESNGQPENN YKTTPPVLDS

401 DGSFFLYSKL TVDKSRWQQG NVFSCSVMHE ALHNHYTQKS LSLSPGK

HEAVY CHAIN (3)
  1 QVQLQESGPG LVKPSETLSL TCTVSGYSIT GGYLWNWIRQ PPGKGLEWIG

51 YISYDGTNNY KPSLKDRVTI SRDTSKNQFS LKLSSVTAAD TAVYYCARYG

101 RVFFDYWGQG TLVTVSSAST KGPSVFPLAP SSKSTSGGTA ALGCLVKDYF

151 PEPVTVSWNS GALTSGVHTF PAVLQSSGLY SLSSVVTVPS SSLGTQTYIC

201 NVNHKPSNTK VDKRVEPKSC DKTHTCPPCP APELLGGPSV FLFPPKPKDT

251 LMISRTPEVT CVVVDVSHED PEVKFNWYVD GVEVHNAKTK PREEQYNSTY

301 RVVSVLTVLH QDWLNGKEYK CKVSNKALPA PIEKTISKAK GQPREPQVYT

351 LPPSREEMTK NQVSLTCLVK GFYPSDIAVE WESNGQPENN YKTTPPVLDS

401 DGSFFLYSKL TVDKSRWQQG NVFSCSVMHE ALHNHYTQKS LSLSPGK

LIGHT CHAIN (4)
  1 DIVMTQSPLS LPVTPGEPAS ISCRSSQSIV HSNGNTYLQW YLQKPGQSPQ

51 LLIYKVSNRL YGVPDRFSGS GSGTDFTLKI SRVEAEDVGV YYCFQGSHVP

101 WTFGQGTKVE IKRTVAAPSV FIFPPSDEQL KSGTASVVCL LNNFYPREAK

151 VQWKVDNALQ SGNSQESVTE QDSKDSTYSL SSTLTLSKAD YEKHKVYACE

201 VTHQGLSSPV TKSFNRGEC
```

In an embodiment of the invention, the light and heavy chains of the anti-IGF1R antibody or antigen-binding fragment thereof comprise one or more disulfide bridges arranged as follows:

| DISULFIDE BRIDGES (CHAIN NUMBER:AMINO ACID NUMBER) |
| --- |
| 1:23 to 1:93 |
| 1:139 to 1:199 |
| 1:219 to 2:220 |
| 2:22 to 2:96 |
| 2:144 to 2:200 |
| 2:261 to 2:321 |
| 2:367 to 2:425 |
| 2:226 to 3:226 |
| 2:229 to 3:229 |
| 3:22 to 3:96 |
| 3:144 to 3:200 |
| 3:261 to 3:321 |
| 3:367 to 3:425 |
| 3:220 to 4:219 |
| 4:23 to 4:93 |
| 4:139 to 4:199 |

In an embodiment of the invention, an immunoglobulin chain that can form anti-IL-23 antibody or antigen-binding fragment thereof that comprises 3 light and/or 3 heavy chain CDRs is selected from:

CDR-L1:
(SEQ ID NO: 9)
KASKKVTIFGSISALH;

CDR-L2:
(SEQ ID NO: 10)
NGAKLES;
and

CDR-L3:
(SEQ ID NO: 11)
LQNKEVPYT;
or

CDR-H1:
(SEQ ID NO: 12)
SYGIT;

CDR-H2:
(SEQ ID NO: 13)
ENYPRSGNTYYNEKFKG;
and

CDR-H3:
(SEQ ID NO: 14)
CEFISTVVAPYYYALDY
or (SEQ ID NO: 15)
SEFISTVVAPYYYALDY
or (SEQ ID NO: 16)

```
                                                   (SEQ ID NO: 17)
AEFISTVVAPYYYALDY
or (SEQ ID NO: 18)
VEFISTVVAPYYYALDY
or (SEQ ID NO: 19)
SEFISTVMAPYYYALDY
or

SEFTSTVVAPYYYALDY
```

In an embodiment of the invention, an immunoglobulin chain that can form part of an anti-IL-23 p19 antibody or antigen-binding fragment thereof comprises an amino acid sequence selected from:

```
Light chain:
                                                   (SEQ ID NO: 20)
DIQMTQSPSSLSASVGDRVTITCRTSENIYSYLAWYQQKPGKAPKLLIYN

AKTLAEGVPSRFSGSGSGTDFTLTISSLQPEDFATYYCQHHYGIPFTFGQ

GTKVEIKR;

Heavy chain:
                                                   (SEQ ID NO: 21)
QVQLVQSGAEVKKPGASVKVSCKASGYIFITYWMTWVRQAPGQGLEWMGQ

IFPASGSADYNEMFEGRVTMTTDTSTSTAYMELRSLRSDDTAVYYCARGG

GGFAYWGQGTLVTVSS;
and

Heavy chain:
                                                   (SEQ ID NO: 22)
QVQLVQSGAEVKKPGASVKVSCKASGYIFITYWMTWVRQAPGQGLEWMGQ

IFPASGSADYAQKLQGRVTMTTDTSTSTAYMELRSLRSDDTAVYYCARGG

GGFAYWGQGTLVTVSS.
```

In an embodiment of the invention, the immunoglobulin comprises 3 heavy and/or 3 light chain CDRs taken from the immunoglobulin chains discussed above.

In an embodiment of the invention, an immunoglobulin that can form part of an anti-IL23 p19 antibody or antigen-binding fragment thereof comprises the following CDRs:

```
CDRH1:
                                                   (SEQ ID NO: 23)
Gly Phe Thr Phe Ser Ser Tyr Thr Met Ser;

CDRH2:
                                                   (SEQ ID NO: 24)
Thr Ile Ser Ser Gly Gly Thr Tyr Thr Tyr Tyr Pro

Asp Ser Val Lys Gly;
and

CDRH3:
                                                   (SEQ ID NO: 25)
Asp Asn His Ala Tyr Asp Arg Gly Pro Phe Phe Asp

Tyr;
or

CDRL1:
                                                   (SEQ ID NO: 26)
Lys Ser Ser Gln Asn Leu Phe Tyr Arg Ser Asn Gln

Lys Asn His Leu Ala;

CDRL2:
                                                   (SEQ ID NO: 27)
Trp Thr Ser Thr Arg Glu Ser;
and CDRL3:
                                                   (SEQ ID NO: 28)
Gln Gln Tyr Tyr Ser Tyr Pro Pro Thr.
```

In an embodiment of the invention, an immunoglobulin that can form part of an anti-IL23 p19 antibody or antigen-binding fragment thereof comprises the following CDRs:

```
CDRH1:
                                                   (SEQ ID NO: 29)
Ala Tyr Gly Met Asp;

CDRH2:
                                                   (SEQ ID NO: 30)
Ser Ile Ser Pro Ser Gly Gly Arg Thr Lys Tyr Ala

Asp Ser Val Lys Gly;
and

CDRH3:
                                                   (SEQ ID NO: 31)
Asp Leu Gly Gly Gly Tyr Tyr Tyr Tyr Tyr Gly Met

Asp Val;
or

CDRL1:
                                                   (SEQ ID NO: 32)
Thr Gly Thr Ser Ser Asp Val Gly Gly Tyr Asn Tyr

Val Ser;

CDRL2:
                                                   (SEQ ID NO: 33)
Glu Val Ser Asn Arg Pro Ser;
and CDRL3:
                                                   (SEQ ID NO: 34)
Ser Ser Tyr Thr Ser Ser Ser Thr Leu Phe Tyr Val.
```

In an embodiment of the invention, an immunoglobulin that can form part of an anti-IL23 p19 antibody or antigen-binding fragment thereof comprises the following CDRs:

```
CDRH1:
                                                   (SEQ ID NO: 35)
GKTFWSWGIN;

CDRH2:
                                                   (SEQ ID NO: 36)
YIYIGTGYTEPNPKYKG;
and CDRH3:
                                                   (SEQ ID NO: 37)
IGGYYGNFAD
or (SEQ ID NO: 38)
IGGYYGNFDQ;
or CDRL1:
                                                   (SEQ ID NO: 39)
RSSQSLLISGGNTYLN;

CDRL2:
                                                   (SEQ ID NO: 40)
LVSKLDQ;
and

CDRL3:
```

-continued

```
                                           (SEQ ID NO: 41)
      WQGTYFPLT.
```

In an embodiment of the invention, an immunoglobulin can form part of an anti-IL23 p19 antibody or antigen-binding fragment thereof comprises any of the immunoglobulins, variable regions thereof or CDRs thereof which are set forth in any of U.S. Pat. Nos. 7,247,711 or 7,491,391; published U.S. application no. US 2007/0218064; or US 2008/0095775; or published PCT application no. WO 2007/024846.

For example, in an embodiment of the invention, an immunoglobulin that can form part of an anti-IL-17 antibody or antigen-binding fragment thereof comprises a heavy and/or light chain immunoglobulin that is selected from those below; or an immunoglobulin chain that can form part of an anti-IL-17 antibody or antigen-binding fragment thereof comprises 3 light and/or 3 heavy chain CDRs from any of the chains set forth below:

```
Light chain:
                                           (SEQ ID NO: 42)
DIVMTQSPLSLPVTPGEPASISCKSSQSLLFSENQKNYLAWYLQKPGQSP

QLLIYWTSTRQSGVPDRFSGSGSGTDFTLKISRVEAEDVGVYYCQQSYYT

PYTFGQGTKVEIKR;
and

Heavy chain:
                                           (SEQ ID NO: 43)
QVQLQESGPGLVKPSETLSLTCTVSGFSLPSHSVSWIRQFPGKGLEWIGI

IWNQGGTDYNSAFKSRVTISVDTSKNQFSLKLSSVTAADTAVYYCARNAY

ITDYYYENYFMDAWGQGTLVTVSS.
```

In an embodiment of the invention, an immunoglobulin that can form part of an anti-HGF antibody or antigen-binding fragment thereof comprises the following 3 light and/or 3 heavy chain CDRs

```
Heavy Chain CDR1
                                           (SEQ ID NO: 44)
a                   TYWMH
```

```
                                           (SEQ ID NO: 45)
b and c             TYWMH;

Heavy Chain CDR2
                                           (SEQ ID NO: 46)
a                   EINPTNGHTNYNEKFKS (SEQ ID NO: 47)
b                   EINPTNGHTNYNPSFQG (SEQ ID NO: 48)
c                   EINPTNGHTNYNQKFQG;
and Heavy Chain CDR3
                                           (SEQ ID NO: 49)
a                   NYVGSIFDY (SEQ ID NO: 50)
b and c             NYVGSIFDY;
or Light (Kappa) Chain CDR1
                                           (SEQ ID NO: 51)
a                   KASENVVSYVS (SEQ ID NO: 52)
b and a             KASENVVSYVS;

Light (Kappa) Chain CDR2
                                           (SEQ ID NO: 53)
a                   GASNRNT (SEQ ID NO: 54)
b                   GASNRNT (SEQ ID NO: 55)
a                   GASNRES;
and Light (Kappa) Chain CDR3
                                           (SEQ ID NO: 56)
a                   GQSYNYPYT (SEQ ID NO: 57)
b and a             GQSYNYPYT.
```

In an embodiment of the invention, the protein is a light or heavy chain immunoglobulin variable chain (either mature (lacking the secretion signal) or unprocessed), optionally linked to an immunoglobulin heavy or light constant chain immunoglobulin, e.g., wherein the variable region comprises an amino acid sequence set forth below, or a mature fragment thereof or wherein the immunoglobulin comprises one or more CDRs (e.g., 3 light chain CDRs or 3 heavy chain CDRs) from those set forth herein (CDRs are underscored):

```
XPA.10.064 light chain
                                                                       (SEQ ID NO: 70)
SYVLTQPPSASGTPGQRVTISCSGSSSNIGINYVYWYQQLPGTAPKLLIYRNDQRPSGVPDRFSGSKSGTSASLAIS

GLRSEDEADYYCATWDDSLSGVVFGGGTKVTVL;

XPA.10.064.03 heavy chain
                                                                       (SEQ ID NO: 71)
EVQLVQSGAEVRKPGASVKVSCKASGYSFTGHYIHWVRQAPGQGLEWMGWINPYSGGTNFPREFQGRVTMTRDTSVN

TVYMELTRLTSDDTSVYYCARDQMVHGGLDYWGQGTLVTVSS;

XPA.10.064.04 heavy chain
```

```
                                                     (SEQ ID NO: 72)
EVQLVQSGAEVRKPGASVKVSCKASGYSFTGHYIHWVRQAPGQGLEWMGWINPYSGGTNFPREFQGRVTMTRDTSVN

TVYMELTRLTSDDTSVYYCARDEMQNGGLDYWGQGTLVTVSS;

XPA.10.064.06 heavy chain
                                                     (SEQ ID NO: 73)
EVQLVQSGAEVRKPGASVKVSCKASGYSFTGHYIHWVRQAPGQGLEWMGWINPYSGGTNFPREFQGRVTMTRDTSVN

TVYMELTRLTSDDTSVYYCARDEMTRGGLDYWGQGTLVTVSS;

XPA.10.064.07 heavy chain
                                                     (SEQ ID NO: 74)
EVQLVQSGAEVRKPGASVKVSCKASGYSFTGHYIHWVRQAPGQGLEWMGWINPYSGGTNFPREFQGRVTMTRDTSVN

TVYMELTRLTSDDTSVYYCARDEMHVGGLDYWGQGTLVTVSS;

XPA.10.064.10 heavy chain
                                                     (SEQ ID NO: 75)
EVQLVQSGAEVRKPGASVKVSCKASGYSFTGHYIHWVRQAPGQGLEWMGWINPYSGGTNFPREFQGRVTMTRDTSVN

TVYMELTRLTSDDTSVYYCARDEMVWGGLDYWGQGTLVTVSS.
```

In an embodiment of the invention, the light chain immunoglobulin is fused to an immunoglobulin constant chain, e.g., a kappa chain or a lambda chain. In an embodiment of the invention, the heavy chain immunoglobulin is fused to an immunoglobulin constant chain, e.g., a gamma-1, gamma-2, gamma-3 or gamma-4 chain.

Other proteins of interest that may be expressed using the methods and 3M cells of the present invention include receptors, ligands, cytokines, chemokines, growth factors, hormones and enzymes.

For example, in an embodiment of the invention, the 3M cell is used to express mature processed or immature, unprocessed MCP1 (e.g., human MCP1) fused to an immunoglobulin gene (e.g., gamma-1, 2, 3 or 4). In an embodiment of the invention, MCP1 is fused to the immunoglobulin by a peptide linker. In an embodiment of the invention, an unprocessed polypeptide sequence of human MCP1 comprises the following amino acid sequence: MKVSAALLCLLLIAATFIPQGLAQPDAINAPVTCCYNFTNRKISVQRLASYRRITSSKCPKEAVIFKTIVAKEICADPKQKWVQDSMDHLDKQTQTPKT (SEQ ID NO: 76). In an embodiment of the invention, a mature polypeptide sequence of human MCP1 comprises the following amino acid sequence: QPDAINAPVTCCYNFTNRKISVQRLASYRRITSSKCPKEAVIFKTIVAKEICADPKQKWVQDSMDHLDKQTQTPKT (SEQ ID NO: 77). In an embodiment of the invention, the immunoglobulin is mature polypeptide sequence of human immunoglobulin heavy chain constant region (hinge to CH3 only), isotype γ1 monomeric variant (C to S mutations in the hinge underscored)

```
                                                     (SEQ ID NO: 78)
VEPKSSDKTHTSPPSPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGK.
```

For example, in an embodiment of the invention, an immunoglobulin that can form part of an anti-PCSK9 antibody (e.g., AX132, AX189 or 1482/1282) or antigen-binding fragment thereof comprises a heavy and/or light chain immunoglobulin that is selected from those below; or an immunoglobulin chain that can form part of an anti-PCSK9 antibody or antigen-binding fragment thereof comprises 3 light and/or 3 heavy chain CDRs from any of the chains set forth below:

```
AX132 VH amino acid sequence:
                                                     (SEQ ID NO: 81)
EVQLLESGGGLVQPGGSLRLSCKASGYTFSSYGMYWVRQAPGKGLEWIGW

IDPGSGGTKYNEKFKGKATISRDNSKNTLYLQMNSLRAEDTAVYYCARER

YGYYFDYWGQGTLVTVSS e.g., wherein the heavy chain comprises the CDRs:

AX132 HCDR1
                                                     (SEQ ID NO: 82)
GYTFSSYGMY

AX132 HCDR2
                                                     (SEQ ID NO: 83)
WIDPGSGGTKYNEKFKG

AX132 HCDR3
ERYGYYFDY
                                                     (SEQ ID NO: 84)

AX132 VL amino acid sequence:
                                                     (SEQ ID NO: 85)
EIVLTQSPATLSLSPGERATITCRASQYVGSYLNWYQQKPGQAPRLLIYD

ASNRATGIPARFSGSGSGTDFTLTISSLEPEDFAVYYCQVWDSSPPVVFG

GGTKVEIK e.g., wherein the light chain comprises the CDRs:

AX132 LCDR1
                                                     (SEQ ID NO: 86)
RASQYVGSYLN

AX132 LCDR2
                                                     (SEQ ID NO: 87)
DASNRAT

AX132 LCDR3
                                                     (SEQ ID NO: 88)
QVWDSSPPVV

AX189 VL amino acid sequence:
                                                     (SEQ ID NO: 89)
DIQMTQSPSSLSASVGDRVTITCRASQDVSRYLTWYQQKPGKAPKLLIYA

ASSLQSGVPSRFSGSGSGTDFTLTISSLQPEDFATYYCQAYDYSLSGYVF

GGGTKVEIK
```

-continued e.g., wherein the light chain comprises the CDRs:

AX189 LCDR1
(SEQ ID NO: 90)
RASQDVSRYLT

AX189 LCDR2
(SEQ ID NO: 91)
AASSLQS

AX189 LCDR3
(SEQ ID NO: 92)
QAYDYSLSGYV

AX189 VH amino acid sequence:
(SEQ ID NO: 93)
EVQLLESGGGLVQPGGSLRLSCKASGYTFSSYWMHWVRQAPGKGLEWIGR

IDPYNGGTKYNEKFKGKATISRDNSKNTLYLQMNSLRAEDTAVYYCARYG

YYLGSYAMDYWGQGTLVTVSS e.g., wherein the heavy chain comprises the CDRs:

AX189 HCDR1
(SEQ ID NO: 94)
GYTFSSYWMH

AX189 HCDR2
(SEQ ID NO: 95)
RIDPYNGGTKYNEKFKG

AX189 HCDR3
(SEQ ID NO: 96)
YGYYLGSYAMDY

1462/1282 heavy chain amino acid sequence:
(SEQ ID NO: 97)
QVQLVQSGAEVKKPGASVKVSCKVS GYTFTDYYMN WVRQAPGQGLEWI

G DINPNNGGAIYNQKFKG RATLTVDKSTSTAYMELRSLRSDDTAVYYC

TS GIITEIAEDF WGQGTLVTVSS e.g., wherein the heavy chain comprises the CDRs:

1462/1282 HCDR1
(SEQ ID NO: 98)
GYTFTDYYMN,

1462/1282 HCDR2
(SEQ ID NO: 99)
DINPNNGGAIYNQKFKG

1462/1282 HCDR3
(SEQ ID NO: 100)
GIITEIAEDF;

1462/1282 light chain amino acid sequence:
(SEQ ID NO: 101)
DIQMTQSPSSLSASVGDRVTITCKASQNVGTNVVWYQQKPGKAPKALIHS

ASYRYSGVPSRFSGSGSGTDFTLTISSLQPEDFATYYCQQYKTYPYTFGQ

GTKVEIKR e.g., wherein the light chain comprises the CDRs:

1462/1282 LCDR1
(SEQ ID NO: 102)
KASQNVGTNVV,

1462/1282 LCDR2
(SEQ ID NO: 103)
SASYRYS

1462/1282 LCDR3
(SEQ ID NO: 104)
QQYKTYPYT.

For example, in a embodiment of the invention, the 3M cell is used to express one or both chains of etanercept (CAS No. 185243-69-0; Drug Bank No. DB00005).

Protein Expression

The processes of the present invention include methods for expressing a polypeptide comprising steps wherein various feeds are added to an initial mammalian 3M cell growth medium. These feeds include hydrolysate feed, vitamin/salt feed, amino acid feed and nutrient feed. The present invention also includes compositions comprising a 3M cell in any of the mediums discussed herein.

The "initial mammalian cell growth medium" can be any of several types of aqueous mediums known in the art; and the meaning of this term would be readily known by any practitioner of ordinary skill in the art. Examples include EX-CELL ACF CHO medium (Sigma-Aldrich (St. Louis, Mo.)). EX-CELL ACF CHO medium is a commercial medium that is animal-component free, with HEPES, without L-glutamine. The medium contains inorganic salts, HEPES and sodium bicarbonate buffers, essential and non-essential amino acids, vitamins, recombinant human insulin, plant hydrolysates, other organic compounds, trace elements, and surfactants. The medium does not contain antibiotics, antimycotics, L-glutamine, or transferring and also contains no animal-derived proteins or other components.

Other examples of initial mammalian cell growth medium include DMEM, DMEM/F-12, F-10 Nutrient Mixture, RPMI Medium 1640, F-12 Nutrient Mixture, Medium 199, Eagle's MEM, RPMI, 293 media, and Iscove's Media. For example, Eagle's minimal essential medium (MEM) comprises L-Arginine hydrochloride (126 mg/l), L-Cystine 2HCl (31 mg/l), L-Histidine hydrochloride-$H_2O$ (42 mg/l), L-Isoleucine (52 mg/l), L-Leucine (52 mg/l), L-Lysine hydrochloride (73 mg/l), L-Methionine (15 mg/l), L-Phenylalanine (32 mg/l), L-Threonine (48 mg/l), L-Tryptophan (10 mg/l), L-Tyrosine disodium salt dehydrate (52 mg/l), L-Valine (46 mg/l), Choline chloride (1 mg/l), D-Calcium pantothenate (1 mg/l), Folic Acid (1 mg/l), Niacinamide (1 mg/l), Pyridoxal hydrochloride (1 mg/l), Riboflavin (0.1 mg/l), Thiamine hydrochloride (1 mg/l), i-Inositol (2 mg/l), Calcium Chloride ($CaCl_2$) (anhyd.) (200 mg/l), Magnesium Sulfate ($MgSO_4$) (anhyd.) (97.67 mg/l), Potassium Chloride (KCl) (400 mg/l), Sodium Bicarbonate ($NaHCO_3$) (2200 mg/l), Sodium Chloride (NaCl) (6800 mg/l), Sodium Phosphate monobasic ($NaH_2PO_4$—$H_2O$) (140 mg/l), D-Glucose (Dextrose) (1000 mg/l) and Phenol Red (10 mg/l).

Modified Eagle Medium (MEM) (2×) comprises L-Arginine hydrochloride (504 mg/l), L-Cystine (96 mg/l), L-Glutamine (870 mg/l), L-Histidine hydrochloride-$H_2O$ (168 mg/l), L-Isoleucine (208 mg/l), L-Leucine (208 mg/l), L-Lysine hydrochloride (290 mg/l), L-Methionine (60 mg/l), L-Phenylalanine (128 mg/l), L-Threonine (192 mg/l), L-Tryptophan (40 mg/l), L-Tyrosine disodium salt dehydrate (208 mg/l), L-Valine (155 mg/l), Choline chloride (4 mg/l), D-Calcium pantothenate (4 mg/l), Folic Acid (4 mg/l), Niacinamide (4 mg/l), Pyridoxal hydrochloride (4 mg/l), Riboflavin (0.4 mg/l), Thiamine hydrochloride (4 mg/l), i-Inositol (8 mg/l), Calcium Chloride ($CaCl_2$) (anhyd.) (285 mg/l), Ferric Nitrate ($Fe(NO_3)_3 \cdot 9H_2O$) (1 mg/l), Magnesium Sulfate ($MgSO_4$) (anhyd.) (195 mg/l), Potassium Chloride (KCl) (800 mg/l), Sodium Bicarbonate ($NaHCO_3$) (8400 mg/l), Sodium Chloride (NaCl) (12800 mg/l), Sodium Phosphate monobasic ($NaH_2PO4$-$H_2O$) (250 mg/l) and D-Glucose (Dextrose) (9000 mg/l).

RPMI Medium 1640 (1×) comprises Glycine (10 mg/l), L-Arginine (200 mg/l), L-Asparagine (50 mg/l), L-Aspartic acid (20 mg/l), L-Cystine 2HCl (65 mg/l), L-Glutamic Acid (20 mg/l), L-Glutamine (300 mg/l), L-Histidine (15 mg/l), L-Hydroxyproline (20 mg/l), L-Isoleucine (50 mg/l), L-Leucine (50 mg/l), L-Lysine hydrochloride (40 mg/l), L-Methionine (15 mg/l), L-Phenylalanine (15 mg/l), L-Proline (20 mg/l), L-Serine (30 mg/l), L-Threonine (20 mg/l), L-Tryptophan (5 mg/l), L-Tyrosine disodium salt dehydrate (29 mg/l), L-Valine (20), Biotin (0.2 mg/l), Choline chloride (3 mg/l), D-Calcium pantothenate (0.25 mg/l), Folic Acid (1 mg/l), Niacinamide (1 mg/l), Para-Aminobenzoic Acid (1 mg/l), Pyridoxine hydrochloride (1 mg/l), Riboflavin (0.2 mg/l), Thiamine hydrochloride (1 mg/l), Vitamin B12 (0.005 mg/l), i-Inositol (35 mg/l), Calcium nitrate ($Ca(NO_3)_2 4H_2O$) (100 mg/l), Magnesium Sulfate ($MgSO_4$) (anhyd.) (48.84 mg/l), Potassium Chloride (KCl) (400 mg/l), Sodium Bicarbonate ($NaHCO_3$) (2000 mg/l), Sodium Chloride (NaCl) (6000 mg/l), Sodium Phosphate dibasic ($Na_2HPO_4$) anhydrous (800 mg/l), D-Glucose (Dextrose) (2000 mg/l) and Glutathione (reduced) (1 mg/l).

Generally, for the purposes of the present invention a "hydrolysate feed" includes wheat and/or soy hydrolysates. Generally, a soy or wheat hydrolysate is the product of an enzymatic digest of soy or wheat and can be purchased commercially. Typically, the hydrolysate is in cell culture grade water and is sterile. In an embodiment of the invention, the hydrolysate is a stock solution at 200 g/liter. In an embodiment of the invention, the hydrolysate is added to the culture medium to reach a final concentration of about 10 g/liter. In an embodiment of the invention, when using either the level 3 process or the enhanced process, the hydrolysate is added to the culture medium either initially, before, with or immediately after inoculation or at about 3 days after inoculation or when viable cell density reaches over about $1 \times 10^6$ cells/ml.

"Viable cell density" refers to the concentration of cells in the medium being analyzed (e.g., cells/ml) which are viable, e.g., capable of growth and replication (e.g., when used to inoculate a liquid culture or a solid culture medium) or capable of excluding a dye such as tryptan blue, eosin or propidium in a dye exclusion assay. Such assays are commonly known in the art.

Generally, for the purposes of the present invention, a "vitamin/salt feed" includes:

| | |
|---|---|
| Sodium selenite | e.g., at a concentration of about $7.13 \times 10^{-4}$ g/liter |
| Adenine sulfate | e.g., at a concentration of about 0.0816 g/liter |
| Adenosine | e.g., at a concentration of about 0.88 g/liter |
| Cytidine | e.g., at a concentration of about 0.88 g/liter |
| Guanosine | e.g., at a concentration of about 0.88 g/liter |
| Uridine | e.g., at a concentration of about 0.88 g/liter |
| Hypoxanthine | e.g., at a concentration of about 0.59 g/liter |
| L-citrulline | e.g., at a concentration of about 0.63 g/liter |
| L-ornithine-HCl | e.g., at a concentration of about 1.28 g/liter |
| Biotin | e.g., at a concentration of about 0.014 g/liter |
| Flavin Adenine Dinucleotide | e.g., at a concentration of about 0.0025 g/liter |
| Folic Acid | e.g., at a concentration of about 0.23 g/liter |
| Lipoic Acid | e.g., at a concentration of about 0.026 g/liter |
| Niacin | e.g., at a concentration of about 1.57 g/liter |
| Pyridoxine HCl | e.g., at a concentration of about 0.15 g/liter |
| Riboflavin | e.g., at a concentration of about 0.093 g/liter |
| Thiamine HCl | e.g., at a concentration of about 0.8 g/liter |
| Vitamin E | e.g., at a concentration of about 0.0188 g/liter |
| Vitamin B12 | e.g., at a concentration of about 0.17 g/liter |
| Choline Chloride | e.g., at a concentration of about 2.51 g/liter |
| Ethanolamine HCl | e.g., at a concentration of about 0.22 g/liter |
| i-Inositol | e.g., at a concentration of about 3.66 g/liter |
| Thymidine | e.g., at a concentration of about 0.39 g/liter |
| Putrescine 2HCl | e.g., at a concentration of about 0.02 g/liter |

-continued

| | |
|---|---|
| Progesterone | e.g., at a concentration of about 0.00075 g/liter; and |
| D-Calcium Pantothenate | e.g., at a concentration of about 1.19 g/liter |

In an embodiment of the invention, the vitamin/salt feed is a 50× stock solution. In an embodiment of the invention, the vitamin/salt feed is added to the culture medium to reach a final concentration of about 20 ml/liter. In an embodiment of the invention, the vitamin/salt feed is added to the culture between days 3 and 5, post-inoculation, or when viable cell density reaches over about $1.2 \times 10^6$ cells/ml.

Generally, for the purposes of the present invention, an "amino acid feed" includes:

| | |
|---|---|
| L-arginine | e.g., at a concentration of about 6.32 g/liter |
| L-cystine | e.g., at a concentration of about 1.7 g/liter |
| L-histidine | e.g., at a concentration of about 2.1 g/liter |
| L-isoleucine | e.g., at a concentration of about 2.6 g/liter |
| L-leucine | e.g., at a concentration of about 2.6 g/liter |
| L-lysine | e.g., at a concentration of about 3.6 g/liter |
| L-Methionine | e.g., at a concentration of about 0.76 g/liter |
| L-phenylalanine | e.g., at a concentration of about 1.65 g/liter |
| L-threonine | e.g., at a concentration of about 2.38 g/liter |
| L-tryptophan | e.g., at a concentration of about 0.51 g/liter |
| L-tyrosine | e.g., at a concentration of about 1.8 g/liter |
| L-valine | e.g., at a concentration of about 2.34 g/liter |
| L-alanine | e.g., at a concentration of about 0.89 g/liter |
| L-asparagine | e.g., at a concentration of about 1.5 g/liter |
| L-aspartic acid | e.g., at a concentration of about 1.33 g/liter |
| L-glutamic acid | e.g., at a concentration of about 1.47 g/liter |
| Glycine | e.g., at a concentration of about 0.75 g/liter |
| L-proline | e.g., at a concentration of about 1.15 g/liter; and |
| L-serine | e.g., at a concentration of about 1.05 g/liter |

In an embodiment of the invention, two separate amino acid feed stock solutions are prepared: a 100× stock solution including L-alanine, L-asparagine, L-aspartic acid, L-glutamic acid, glycine, L-proline and L-serine at the concentrations set forth above; and and a 50× solution including L-arginine, L-cystine, L-histidine, L-isoleucine, L-leucine, lysine, L-Methionine, L-phenylalanine, L-threonine, L-tryptophan, L-tyrosine, and L-valine at the concentrations set forth above. These stocks can be made and added separately to the culture medium. In an embodiment of the invention, the amino acid stock solution is added to the initial medium at day 0, before, with or immediately after cell inoculation.

Generally, for the purposes of the present invention, a "nutrient feed" includes:

| | |
|---|---|
| L-asparagine: | e.g., at a concentration of about 40.6 g/liter |
| L-proline | e.g., at a concentration of about 10.81 g/liter |
| L-isoleucine | e.g., at a concentration of about 18.53 g/liter |
| L-cysteine-HCl | e.g., at a concentration of about 11.19 g/liter |
| L-leucine | e.g., at a concentration of about 16.58 g/liter |
| L-threonine | e.g., at a concentration of about 8.2 g/liter |
| L-tyrosine | e.g., at a concentration of about 9.9 g/liter |
| L-arginine | e.g., at a concentration of about 9.29 g/liter |
| L-aspartic acid | e.g., at a concentration of about 3.56 g/liter |
| L-glutamic acid | e.g., at a concentration of about 6.28 g/liter |
| Glycine | e.g., at a concentration of about 2.83 g/liter |
| L-histidine | e.g., at a concentration of about 6.23 g/liter |
| L-methionine | e.g., at a concentration of about 6.58 g/liter |
| L-tryptophan | e.g., at a concentration of about 4.93 g/liter |
| L-lysine | e.g., at a concentration of about 14.66 g/liter |
| L-phenylalanine | e.g., at a concentration of about 8.64 g/liter |
| L-valine | e.g., at a concentration of about 13.08 g/liter |
| L-serine: | e.g., at a concentration of about 13 g/liter |
| Sodium phosphate monobasic: | e.g., at a concentration of about 14.41 g/liter |

| | |
|---|---|
| Zinc sulfate: | e.g., at a concentration of about 0.054 g/liter |
| Cupric sulfate: | e.g., at a concentration of about 0.00016 g/liter |
| Ammonium vanadate: | e.g., at a concentration of about 0.000039 g/liter |
| Cobalt chloride: | e.g., at a concentration of about 0.000125 g/liter |
| Nickel dichloride hexahydrate: | e.g., at a concentration of about 0.00002 g/liter |
| Sodium molybdate dehydrate: | e.g., at a concentration of about 0.000008 g/liter |
| Tin chloride dehydrate: | e.g., at a concentration of about 0.000004 g/liter |
| Manganese chloride tetrahydrate: | e.g., at a concentration of about 0.000015 g/liter |

In an embodiment of the invention, the nutrient feed is a 50× stock solution. In an embodiment of the invention, the nutrient feed is added to the culture medium to reach a final concentration of about 20 ml/liter. In an embodiment of the invention, the nutrient feed is added to the culture between days 3 and 5, post-inoculation, or when viable cell density reaches about $1.2 \times 10^6$ cells/ml.

Furthermore, in an embodiment of the invention, glucose (from a 2.5 M stock solution) and L-glutamine (from a 0.2 M stock solution) are added to the culture medium at any point, e.g., when the concentration of the nutrients fall below 1.5 g/liter glucose and/or 150 mg/liter L-glutamine.

The present invention also includes processes wherein the osmolality and/or the temperature of the culture is optionally shifted. The osmolality or temperature shift may be done at any point in-process.

The osmolality shift has been shown to increase culture specific productivity as well as cell viability. Typically, the initial mammalian cell growth medium has a starting osmolality of about 300 mOsm. The "osmolality shift" of the present invention, however, includes shifting the culture osmolality to from about 400 mOsM to about 500 mOsm.

Osmolality is a measure of the osmoles of solute per kilogram of solvent. Osmolality can be measured using an osmometer which measures colligative properties, such as freezing-point depression, vapor pressure, or boiling-point elevation.

Osmolality of a cell culture may be shifted by any of several means. For example, a concentrated salt solution (e.g., including 5M NaCl salts stock, 8-12 mL/L added), soy hydrolysate solution (200 g/L stock, 50-80 mL/L added), sodium carbonate or sodium bicarbonate or carbon dioxide may be added. In an embodiment of the invention, adding the nutrient feed to the medium shifts the osmolality.

In an embodiment of the invention, the temperature of the culture is optionally shifted, e.g., in a step change, from about 36.5° C. (±0.5° C.) to between about 33° C. and 35° C.

Vectors, such as plasmids, including a gene to be expressed by a process of the present invention, e.g., an immunoglobulin chain such as any of those discussed herein, may be introduced into a 3M host cell by any of several methods known in the art. Transformation can be carried out, e.g., by the calcium phosphate precipitation method as described by Graham and Van der Eb, Virology, 52: 546 (1978). Other methods for introducing DNA into 3M cells such as by nuclear injection or by protoplast fusion may also be used. Methods for transformation also include electroporation, liposomal transformation and DEAE-Dextran transformation.

Host 3M cells comprising a gene to be expressed using a process of the present invention may be further selected and screened to identify the clone with the requisite characteristics for expression of a target gene. One common approach, to achieve maximal expression, involves the use of mutant cell lines and a gradual increase in the selection pressure over several months for a co-transfected selection marker such as dihydrofolate reductase (DHFR) (Kaufman et al. (1982) J. Mol. Biol. 159: 601-621; Schimke et al. (1982) Natl. Cancer Inst. Monogr. 60: 79-86). In order to achieve high production rates, a dihydrofolate reductase (DHFR) negative cell line (e.g., a CHO cell line) (Urlaub et al. (1980) Proc. Natl. Acad. Sci. USA 77: 4216-4220) is transformed with an expression vector containing a functional DHFR gene in combination with the target gene to be expressed. Amplification of the vector-inserted target genes occurs in response to addition of increasing amounts of the DHFR antagonist methotrexate (MTX) to the culture medium and clones or subpopulations carrying multiple copies of the recombinant genes are generated and can be selected (Wurm (1990) Biologicals 18:159-164). The gene amplification process typically takes several months until stable cell lines are obtained which show high target gene copy numbers and high production rates of the desired protein. 3M cells comprising a DHFR gene, as well as cells that have undergone amplification of DHFR and a target gene (e.g., an immunoglobulin gene) form part of the invention. In an embodiment of the invention, 3M cells have not undergone any amplification (e.g., DHFR amplification). In an embodiment of the invention, target genes to be expressed from the 3M cells exist in only about one copy per cell.

In an embodiment of the invention, a polynucleotide, e.g., encoding an immunoglobulin chain and/or a DHFR gene, is integrated into 3M host cell chromosomal DNA or is in a vector that is ectopic and autonomously replicating. In an embodiment of the invention, the polynucleotide of the present invention is present in the 3M cell at several copies per cell (e.g., 2, 3, 4, 5, 6, 7, 8, 9, 10, 15, 20). Where an expression vector has been integrated into the genomic DNA of the host 3M cell to improve stability, the copy number of the vector DNA, and, concomitantly, the amount of product which could be expressed, can be increased by selecting for cell lines in which the vector sequences have been amplified after integration into the DNA of the host cell. Integrated genes may be screened for the presence and relative amount of chromosomaily incorporated DNA and corresponding mRNA and polypeptide synthesis by standard methods. For example, the presence of the desired integrate may be detected by standard procedures such as DNA sequencing, Southern blotting, Northern blotting and/or Western blotting.

A 3M cell line may also be stored in a master cell bank (MCB) and/or working cell bank (WCB). Typically, when a cell line is to be used over many manufacturing cycles, a two-tiered cell banking system consisting of a master cell bank or master seed bank (MSB) and a working cell bank can be established. A cell line is established from a single host cell clone and this cell line is used to make-up the MCB. Generally, this MCB must be characterized and extensively tested for contaminants such as bacteria, fungi, viruses and mycoplasma. A sample of cells from the MCB can be expanded to form the WCB, which is characterized for cell viability prior to use in a manufacturing process. The cells in a MCB or WCB can be stored in vials, for example, at low temperature (e.g., 0° C. or lower, –20° C. or –80° C.).

Methods for expressing a polypeptide, e.g., an immunoglobulin, using a 3M cell of the present invention comprises, in an embodiment of the present invention:

1—Expanding 3M cells expressing the polypeptide in a standard initial mammalian growth medium.

This expansion can be done, for example, in shake flasks. In an embodiment of the invention, expansion occurs by growth to about $1-2 \times 10^6$ cells/ml, dilution of a sample of those cells (e.g., to a density of about $2.5$-$5\times10^5$ cells/ml) and, then, regrowth to about $1$-$2\times10^6$ cells/ml, for about 10-30 cycles.

2—inoculating an initial mammalian cell growth medium with the expanded 3M cells, to a cell density of about $2.5$-$5\times10^5$ cells/ml, and adding supplements to the medium. The supplements are soy and/or wheat hydrolysate, amino acid feed, vitamin/salt feed, nutrient feed, glucose and L-glutamine.

The day of inoculation is "day 0", the following day is "day 1", the following day is "day 2", and so on.

Soy and/or wheat hydrolysates are added, for example, either on day 0 or after viable cell density has reached over about $10^6$ cells/ml. In an embodiment of the invention, the hydrolysate(s) are simply added on day 3.

Amino acid feeds (discussed herein) are added, for example, at day 0, e.g., to reach approximate final culture concentrations as set forth below (not including the concentration of any indicated component from other sources such as from the initial mammalian cell growth medium):

| Component | Final concentration in culture (mg/liter) |
| --- | --- |
| L-arginine | 126.4 |
| L-cystine | 34 |
| L-histidine | 42 |
| L-isoleucine | 52 |
| L-leucine | 52 |
| L-lysine | 72 |
| L-Methionine | 15.2 |
| L-phenylalanine | 33 |
| L-threonine | 47.6 |
| L-tryptophan | 10.2 |
| L-tyrosine | 36 |
| L-valine | 46.8 |
| L-alanine | 8.9 |
| L-asparagine | 30 |
| L-aspartic acid | 26.6 |
| L-glutamic acid | 29.4 |
| Glycine | 15 |
| L-proline | 23 |
| L-serine | 21 |

In an embodiment of the invention, amino acid feeds are not added to the medium.

Vitamin/salt feed solution (discussed above) is added, for example, between days 3 and 5 or when viable cell density reaches about $1.2\times10^6$ cells/ml, e.g., to reach approximate final culture concentrations set forth below (not including the concentration of any indicated component from other sources such as from the initial mammalian cell growth medium):

| Component | Final culture concentrations (mg/liter) |
| --- | --- |
| Sodium selenite | 0.01426 |
| Adenine sulfate | 1.632 |
| Adenosine | 17.6 |
| Cytidine | 17.6 |
| Guanosine | 17.6 |
| Uridine | 17.6 |
| Hypoxanthine | 11.8 |
| L-citrulline | 12.6 |
| L-ornithine-HCl | 25.6 |
| Biotin | 0.28 |
| Flavin Adenine Dinucleotide | 0.05 |
| Folic Acid | 4.6 |
| Lipoic Acid | 0.52 |
| Niacin | 31.4 |
| Pyridoxine HCl | 3 |
| Riboflavin | 1.86 |
| Thiamine HCl | 16 |

-continued

| Component | Final culture concentrations (mg/liter) |
| --- | --- |
| Vitamin E | 0.376 |
| Vitamin B12 | 3.4 |
| Choline Chloride | 50.2 |
| Ethanolamine HCl | 4.4 |
| i-Inositol | 73.2 |
| Thymidine | 7.8 |
| Putrescine 2HCl | 0.4 |
| Progesterone | 0.015 |
| D-Calcium Pantothenate | 23.8 |

Some components of the vitamin/salt feed are also in other feeds such as the amino acid feed. These final culture concentrations are of the components from the vitamin/salt feed and do not reflect the cumulative concentrations of the indicated components from both the amino acid feed and the vitamin/salt feed.

Nutrient feed (discussed herein) is added, for example, between days 3 and 5 or when viable cell density reaches about $1.2\times10^6$ cells/ml, e.g., to reach approximate final culture concentrations set forth below (not including the concentration of any indicated component from other sources such as from the initial mammalian cell growth medium or amino acid feed):

| Component | Final culture concentration (mg/liter) |
| --- | --- |
| L-asparagine: | 812 mg/liter |
| L-proline | 216 mg/liter |
| L-isoleucine | 370 mg/liter |
| L-cysteine-HCl | 224 mg/liter |
| L-leucine | 332 mg/liter |
| L-threonine | 164 mg/liter |
| L-tyrosine | 198 mg/liter |
| L-arginine | 186 mg/liter |
| L-aspartic acid | 71 mg/liter |
| L-glutamic acid | 126 mg/liter |
| Glycine | 57 mg/liter |
| L-histidine | 125 mg/liter |
| L-methionine | 132 mg/liter |
| L-tryptophan | 99 mg/liter |
| L-lysine | 293 mg/liter |
| L-phenylalanine | 174 mg/liter |
| L-valine | 262 mg/liter |
| L-serine: | 260 mg/liter |
| Sodium phosphate monobasic: | 288.2 mg/liter |
| Zinc sulfate: | 1.08 mg/liter |
| Cupric sulfate: | 0.0032 mg/liter |
| Ammonium vanadate: | 0.00078 mg/liter |
| Cobalt chloride: | 0.0025 mg/liter |
| Nickel dichloride hexahydrate: | 0.0004 mg/liter |
| Sodium molybdate dehydrate: | 0.00016 mg/liter |
| Tin chloride dehydrate: | 0.00008 mg/liter |
| Manganese chloride tetrahydrate: | 0.0003 mg/liter |

Some components of the nutrient feed are also in other feeds such as the amino acid feed. These final culture concentrations are of the components from the nutrient feed and do not reflect the cumulative concentrations of the indicated components from both the amino acid feed and the nutrient feed.

Glucose is added, for example, when the glucose concentration in the culture medium falls below about 1.5 g/liter and L-glutamine is added, for example, when the glutamine concentration in the culture medium fails below about 150 mg/liter.

3—Optionally, harvesting the 3M cells from the production cell culture medium, e.g., when viability is below about 60%, by removing the cells from the culture medium (e.g., by lowering the temperature of the cells to about 15° C., adding sodium-phosphate buffer to stabilize the pH at about 6.8 and centrifuging the culture medium to clarify it of cells). If the protein is secreted, the medium can be retained for further processing, if the protein is not secreted, the 3M cells can be retained for further processing.

Any of several methods can be used to remove the 3M cells from the medium, e.g., by centrifugation. For example, using a continuous disk-stack centrifuge, e.g., with a flow rate/sigma (cm/sec) of about $9.27 \times 10^{-7}$.

Furthermore, the medium can be filtered to remove 3M cells, e.g., by depth filtration with or without a centrifuge. For example, with a centrifuge, the process can, in an embodiment of the invention, comprise use of an 8±2 L broth/ft² filter (e.g., charged cellulose filter); without a centrifuge, the process can, in an embodiment of the invention, comprise use of a 20±3 L broth/ft² filter.

In addition, the medium can be filtered through a fine filter, for example, with a 0.2 micron pore size (e.g., a PVDF filter). and;

4—Optionally further purifying the protein, e.g., antibody, for example, chromatographically.

Optionally, the osmolality of the culture is shifted to about 400 mOsm to about 500 mOsm (discussed herein). In an embodiment of the invention, this shift occurs when the cells are at a density of at or above $1 \times 10^6$ cells/ml.

Optionally, the temperature of the 3M cell culture temperature is shifted to 33° C. to about 35° C. (discussed herein). In an embodiment of the invention, this shift occurs, between days 4 and 8, e.g., when the change in viable cell density over a 24 hour period is less than 10%.

In an embodiment of the invention, the 3M cell culture $O_2$ concentration, pH and temperature conditions are continuously monitored and adjusted during cell growth. In an embodiment of the invention, $O_2$ concentration is monitored and maintained at about 60% during cell growth; and/or pH is continuously monitored and maintained at about 6.8 (e.g., ±0.02) during cell growth; and/or temperature is continuously monitored and maintained at about 36.5° C. (e.g., about ±0.5° C.) during cell growth 3M cell growth can be performed in any of several systems. For example, cell growth can be done in a simple flask, e.g., a glass shake flask. Other systems include tank bioreactors, bag bioreactors and disposable bioreactors. A tank bioreactor includes, typically, a metal vessel (e.g., a stainless steel jacketed vessel) in which cells are grown in a liquid medium. Tank bioreactors can be used for a wide range of culture volumes (e.g., 100 l, 150 l, 10000 l, 15000 l). Tank bioreactors often have additional features for controlling cell growth conditions, including means for temperature control, medium agitation, controlling sparge gas concentrations, controlling pH, controlling $O_2$ concentration, removing samples from the medium, reactor weight indication and control, cleaning hardware, sterilizing the hardware, piping or tubing to deliver all services, adding media, control pH, control solutions, and control gases, pumping sterile fluids into the growth vessel and, supervisory control and a data acquisition. Classifications of tank bioreactor include stirred tank reactors wherein mechanical stirrers (e.g., impellers) are used to mix the reactor to distribute heat and materials (such as oxygen and substrates). Bubble column reactors are tall reactors which use air alone to mix the contents. Air lift reactors are similar to bubble column reactors, but differ by the fact that they contain a draft tube. The draft tube is typically an inner tube which improves circulation and oxygen transfer and equalizes shear forces in the reactor. In fluidized bed reactors, cells are "immobilized" on small particles which move with the fluid. The small particles create a large surface area for cells to stick to and enable a high rate of transfer of oxygen and nutrients to the cells. In packed bed reactors cells are immobilized on large particles. These particles do not move with the liquid. Packed bed reactors are simple to construct and operate but can suffer from blockages and from poor oxygen transfer. A disposable bioreactor is a disposable, one-time use bioreactor. Often, disposable bioreactors possess features similar to non-disposable bioreactors (e.g., agitation system, sparge, probes, ports, etc.).

The present invention includes any liquid culture medium, comprising one or more 3M cells, generated by any of the processes set forth herein, including 3M containing culture mediums generated as intermediates during practice of any of the cell culture methods discussed herein; for example, produced by a process comprising inoculating an initial mammalian cell growth medium, pre-warmed to about 37° C.; which medium comprises HEPES, sodium bicarbonate buffers, inorganic salts, non-essential amino acids, recombinant human insulin, trace elements and surfactants; and which does not comprise L-glutamine, antibiotics, antimycotics or animal-derived components; with 3M cells expressing an antibody light chain immunoglobulin and heavy chain immunoglobulin, to a cell density of about $2.5\text{-}5 \times 10^6$ cells/ml; and, adding the following supplements to the medium before, simultaneously with or immediately after said inoculation: soy hydrolysate to a final concentration of about 10 g/liter; and, optionally, an amino acid feed wherein the concentration of the components added by said amino acid feed are approximately those set forth below:

| | |
|---|---|
| L-arginine: | 126.4 mg/liter |
| L-cystine: | 34 mg/liter |
| L-histidine: | 42 mg/liter |
| L-isoleucine: | 52 mg/liter |
| L-leucine: | 52 mg/liter |
| L-lysine: | 72 mg/liter |
| L-Methionine: | 15.2 mg/liter |
| L-phenylalanine: | 33 mg/liter |
| L-threonine: | 47.6 mg/liter |
| L-tryptophan: | 10.2 mg/liter |
| L-tyrosine: | 36 mg/liter |
| L-valine: | 46.8 mg/liter |
| L-alanine: | 8.9 mg/liter |
| L-asparagine: | 30 mg/liter |
| L-aspartic acid: | 26.6 mg/liter |
| L-glutamic acid: | 29.4 mg/liter |
| glycine: | 15 mg/liter |
| L-proline: | 23 mg/liter |
| L-serine: | 21 mg/liter; | and, when viable cell density reaches over about $1.2 \times 10^6$ cells/ml, adding supplement feeds wherein the concentration of the components added by said supplement feeds are approximately those set forth below:

| | |
|---|---|
| Sodium selenite: | 0.01426 mg/liter |
| Adenine sulfate: | 1.632 mg/liter |
| Adenosine: | 17.6 mg/liter |
| Cytidine: | 17.6 mg/liter |
| Guanosine: | 17.6 mg/liter |
| Uridine: | 17.6 mg/liter |
| Hypoxanthine: | 11.8 mg/liter |
| L-citrulline: | 12.6 mg/liter |
| L-ornithine-HCl: | 25.6 mg/liter |
| Biotin: | 0.28 mg/liter |
| Flavin Adenine Dinucleotide: | 0.05 mg/liter |

-continued

| | |
|---|---|
| Folic Acid: | 4.6 mg/liter |
| Lipoic Acid: | 0.52 mg/liter |
| Niacin: | 31.4 mg/liter |
| Pyridoxine HCl: | 3 mg/liter |
| Riboflavin: | 1.86 mg/liter |
| Thiamine HCl: | 16 mg/liter |
| Vitamin E: | 0.376 mg/liter |
| Vitamin B12: | 3.4 mg/liter |
| Choline Chloride: | 50.2 mg/liter |
| Ethanolamine HCl: | 4.4 mg/liter |
| i-Inositol: | 73.2 mg/liter |
| Thymidine: | 7.8 mg/liter |
| Putrescine 2HCl: | 0.4 mg/liter |
| Progesterone: | 0.015 mg/liter |
| D-Calcium Pantothenate: | 23.8 mg/liter |
| L-asparagine: | 812 mg/liter |
| L-proline | 216 mg/liter |
| L-isoleucine | 370 mg/liter |
| L-cysteine-HCl | 224 mg/liter |
| L-leucine | 332 mg/liter |
| L-threonine | 164 mg/liter |
| L-tyrosine | 198 mg/liter |
| L-arginine | 186 mg/liter |
| L-aspartic acid | 71 mg/liter |
| L-glutamic acid | 126 mg/liter |
| Glycine | 57 mg/liter |
| L-histidine | 125 mg/liter |
| L-methionine | 132 mg/liter |
| L-tryptophan | 99 mg/liter |
| L-lysine | 293 mg/liter |
| L-phenylalanine | 174 mg/liter |
| L-valine | 262 mg/liter |
| L-serine: | 260 mg/liter |
| Sodium phosphate monobasic: | 288.2 mg/liter |
| Zinc sulfate: | 1.08 mg/liter |
| Cupric sulfate: | 0.0032 mg/liter |
| Ammonium vanadate: | 0.00078 mg/liter |
| Cobalt chloride: | 0.0025 mg/liter |
| Nickel dichloride hexahydrate: | 0.0004 mg/liter |
| Sodium molybdate dehydrate: | 0.00016 mg/liter; | and, during cell growth, adding glucose to the medium when glucose levels fall below about 1.5 g/liter and adding L-glutamine when L-glutamine levels fall below about 150 mg/liter; and during cell growth maintaining $O_2$ concentration at about 60%; pH at about 6.8±0.02 and temperature at about 36.5° C.±0.5° C.; for example, wherein the medium comprises cells that have reached about 60% viability.

EXAMPLES

The present invention is intended to exemplify the present invention and not to be a limitation thereof. Any method or composition disclosed below falls within the scope of the present invention.

Example 1

Generation of 3M Cell Line

Previous unsuccessful attempts were made to pre-adapt CHO host cell lines for efficient growth in serum free media. One attempt was made to gradually adapt host cells into IS-CHO-V (a commercially available cell culture medium containing no animal components; available from Irvine Scientific; Santa Ana, Calif.) serum-free medium in suspension for 56 days and then re-adapt back to serum-containing medium in attachment. The cell line was named DXB-IS-A (also known as ISA).

In another attempt, a new serum-free protein-free media formulation, C5467, developed by Sigma-Aldrich Inc. was adapted to scale up antibody production for select clones. Therefore, the attempt was made to gradually adapt host cells into Sigma C5467 medium in suspension for 41 days and then re-adapt back to serum-containing medium in attachment. The cell line generated with this method was named DXB-Sig-A. This cell line was compared with ISA. The cell growth and viability, during suspension adaptation into C5467 medium, of the transfected cell lines derived from DXB-Sig-A and of the ISA cell line, were compared. However, the DXB-Sig-A cell line was found to be even harder than ISA to adapt into the C5467 medium.

Additionally, an attempt was made to simulate the newly developed strategy by abruptly adapting host cells into modified Sigma C5467 medium in suspension for 83 days. The cell line generated with this method was named DXB host (3 mo). This new cell line performed about the same as ISA. Cell growth and viability during suspension adaptation into modified C5467, of the transfected cell lines derived from the DXB host (3 mo) and of the ISA cell line, were compared.

It was concluded that a new approach, other than mere serum-free adaptation, was needed to make these cells more robust. The approach of the present invention was performed by subcloning the DXB host (3 mo) into C5467 medium in 96 well plates twice to ensure purity, recoverability, stability, and consistency in performance in serum-free environment. The new cell line that was made, 3M (also known as "DXBHost 2×Susp"), was found to be superior to ISA when transformed with anti-IL23, anti-HGF, or cyno-anti-TSLP expression constructs, in terms of cell growth, clone recovery, and the rate of successful clones growing and producing desirable amounts of antibody in serum-free suspension conditions.

Materials & Methods

Cell Thawing. To revive DXB11 CHO host (3 mo) cells for expansion, a frozen vial was partially submerged into a 37° C. circulating water bath until the content just thawed (about 1-2 min). The content was then transferred into a T75 flask with 20 ml host medium and then grown. A medium exchange with fresh host medium was performed the next day.

Subcloning. When cells in the T75 flask reached about 90% confluency, cells were trypsinized and resuspended in 8 ml of host medium. Four ml of the cell suspension was centrifuged at 1000 rpm for 15 minutes. The cell pellet was resuspended with 4 ml of serum-free host medium and 100 ul of cell suspension was two-fold serial diluted across each well in the 8 rows of a 96 well plate containing 100 ul of medium in each well. Each well of the 96-well plate was supplemented with additional 100 ul of fresh serum-free host medium. The plates were incubated at 37° C. in a 7.5% $CO_2$ incubator with high humidity for 2 weeks. Cells from the wells at the dilution end point of each row were harvested and were transferred to T25 flasks containing 2 ml of serum-free host media. The T-25 flasks were maintained in a 37° C. incubator with 7.5% $CO_2$ and were agitated at 70 rpm on an orbital shaker for one week. Cells from T-25 flasks were subcloned into 96-well plates and scaled up again to T25 flasks with the procedures described above.

Cell Expansion. Two ml of cells in T25 flask were transferred into a T75 flask with 5 ml of serum-free host media and were agitated at 70 rpm for 4 days. Cells were then transferred into shake flasks to scale up, i.e., 18 ml for 125-ml flask, 45 ml for 250-ml flask, and 135 ml for 500-ml flask, and were agitated at 105 rpm.

Cell Bank Preparation. When the cells in the 500-ml shake flask reached a density of $1.7 \times 10^6$ cells/ml, cells were harvested and centrifuged at 1000 rpm for 10 minutes. Cell pellets were resuspended in 20 ml of freezing medium. Cells were aliquoted into twenty 1.8 ml CryoTubes, loaded into a freezing container and placed in a −80° C. freezer overnight. Frozen vials were then transferred into a liquid nitrogen freezer for long-term storage.

TABLE 1

List of Media (See Table 2 for the List of Components or Chemicals)

| Medium Name | Components |
|---|---|
| Growth medium (general term for the media used to grow host cells or transfected cells, either in adherent or suspension mode.) | Growth medium could be host medium or serum-free host medium. |
| Host medium | MEMα+ with 10% cFBS |
| Serum-free host medium | JRH ImMEDIAte ADVANTAGE 65778 with 40 ml/L glutamine, 10 ml/L HT, 20 ml/L GSEM, 1 ml/L Trace A, 1 ml/L Trace B, 1 m1/L CD Lipid, 1 ml/L Mix 1 |
| Freezing medium | Growth medium (add 10% serum if serum-free) + 10% DMSO |

TABLE 2

List of Materials Used

| Component or Chemical Name | Comments |
|---|---|
| MEMα+ = Minimum Essential Medium with nucleotides and nucleosides | (Gibco CAT# 12571-063) |
| cFBS* = Characterized Fetal Bovine Serum, γ-irradiated | HyClone CAT# SH30071.03 |
| JRH ImMEDIAte ADVANTAGE 65778 = SAFC C5467-44 (w/o ATA (aurine tricarboxylic acid), w/o L-Glutamine). | SAFC CAT# 65778-1000M3367 |
| Glucose 45% solution | Sigma CAT# G8769 |
| Glutamine (200 mM) | Gibco CAT# 25030-081 |
| HT = HT Supplement (100X) - mixture of sodium hypoxanthine and thymidine | Gibco CAT# 11067-030 |
| GSEM = GSEM Supplement (50X) | SIGMA CAT# G9785 |
| Mix 1 = CHO Kit 2 Iron Chelator | SIGMA |
| Trace A = Trace Elements A (1000X) | Cellgro CAT# 99-182-C |
| Trace B = Trace Elements B (1000X) | Cellgro CAT# 99-175-CI |
| CD Lipid = Chemically Defined Lipid Concentrate | Gibco CAT# 11905-031 |
| Trypsin = Trypsin-EDTA (1X) | Gibco CAT# 25300-054 |
| DMSO = Dimethyl Sulphoxide | Sigma CAT# 2650 |

Trace Elements A (1000×)
1.6 mg/l $CuSO_4.5H_2O$
863.00 mg/l $ZnSO_4.7H_2O$
17.30 mg/l Selenite.2Na
1155.10 mg/l Ferric citrate
Trace Elements B (1000×)
0.17 mg/l $MnSO_4.H2O$
140.00 mg/l $Na_2SiO_3.9H_2O$
1.24 mg/l Molybdic acid, Ammonium salt
0.65 mg/l $NH_4VO_3$
0.13 mg/l $NiSO_4.6H_2O$
0.12 mg/l SnCl(anhydrous)
Chemically Defined Lipid Concentrate
2 mg/l Arachidonic Acid
220 mg/l Cholesterol
70 mg/l DL-alpha-Tocopherol Acetate
100% Ethyl Alcohol
10 mg/l Linoleic Acid
10 mg/l Linolenic Acid
10 mg/l Myristic Acid
10 mg/l Oleic Acid
10 mg/l Palmitic Acid
10 mg/l Palmitoleic Acid
90000 mg/l Pluronic F-68
10 mg/l Stearic Acid
2200 mg/l Tween 80®
GSEM Supplement
450.0 mg/l L-alanine; 4261.0 mg/l L-asparagine.$H_2O$; 650.0 mg/l L-aspartic acid; 3750.0 mg/l L-glutamic acid; 575.0 mg/l L-proline; 500.0 mg/l L-serine; 350.0 mg/l adenosine; 350.0 mg/l Guanosine; 350.0 mg/l Cytidine; 350.0 mg/l uridine; and 12.0 mg/l thymidine.

TABLE 3

Lab Equipment and Supplies

| Lab Equipments and Supplies | Catalog, Part, or Model Number |
|---|---|
| CEDEX Counter = CEDEX Automated Cell Culture Analyzer | Innovatis |
| 7.5% $CO_2$ incubator | Forma Scientific Model # 3950 |
| Orbital shaker | Forma Scientific Model # 416 |
| Allegra-6R benchtop centrifuge | Beckman Model # 366816 |
| −80° C. Biofreezer | Forma Scientific Model # 8584 |
| Liquid nitrogen Cryo plus 3 freezer | Forma Scientific Model # 7404 |
| Circulating water bath | Precision Model # 51221035 |
| 96-well plates | Falcon Cat # 353072 |
| T-25 flasks | Corning Cat # 430639 |
| T-75 flasks | Corning Cat # 430725 |
| 125 ml shake flask | Corning Cat # 431143 |
| 250 ml shake flask | Corning Cat # 431144 |
| 500 ml shake flask | Corning Cat # 431145 |
| 1 L shake flask | Corning Cat # 431147 |
| 1.8 ml CryoTube | Nunc Cat # 368632 |
| 15 ml-conical tube | Falcon Cat # 352097 |
| freezing container = Controlled rate freezing container = .Mr. Frosty. | Nalgene Cat # 5100-0001 |

Results and Discussion

The 3M (DXBHost 2×Susp) cell line was compared with the old standard host cell line ISA (DXB-IS-A) in the performance of cell growth potential and antibody production. The cell growth potential was evaluated at the host cell stage (i.e., before transfection and subcloning) to avoid clonal variations. The antibody production potential of these two cell lines was evaluated at the cloning stage (i.e., after 19-days of incubation in 96-wells after transfection) and also after adaptation into suspension in serum-free media.

3M had better cell growth potential than ISA. Both 3M and ISA cells were seeded at $0.5×10^6$ cells/ml with 60 ml serum-free host medium in 250-ml shake flasks. The flasks were agitated at 105 rpm until cell viability reached just below 40%. In batch mode (as shown in FIG. 1), 3M cells reached higher cell density ($2.3×10^6$ cells/ml vs. $1.7×10^6$ cells/ml) and lasted for a longer culture time (20 days vs. 10 days) than ISA cells. This means that 3M cells were more robust than ISA cells in serum-free suspension conditions. In theory, if specific antibody productivity is the same for both cell lines after transfection, 3M would produce more antibody than ISA due to higher density and longevity of cells.

Figure 2:
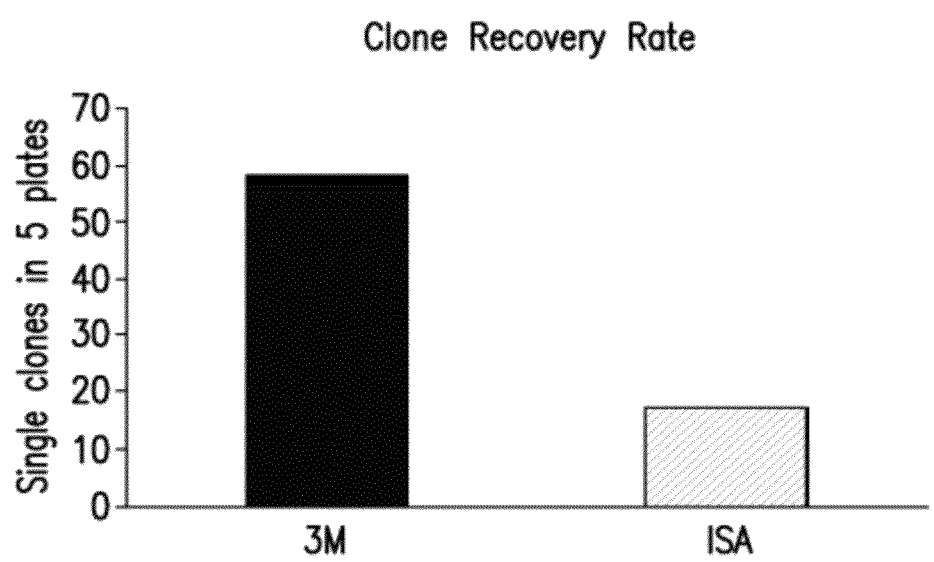
FIG. 2. Cell recovery efficiency after transfection for murine anti-IL17 project.

The cloning recovery efficiency of 3M and ISA cell lines was compared after transfection with vectors encoding murine anti-IL17 immunoglobulin chains. This was done by counting the number of clones, including multiple clones in single wells, recovered from five 96-well plates with the same seeding cell density. As shown in FIG. 2, the number of clones recovered from five 96 well plates were 58 for 3M and only 17 for ISA. Multiple-clone counting was performed only once. 3M had better cloning recovery efficiency than ISA in all other projects (i.e., anti-IL23 antibody, anti-hepatocyte growth factor and cyno anti-TSLP).

Both 3M and ISA cells were transfected using the vectors containing cDNAs for selection markers (i.e., dhfr & hygromycin B resistance) and for antibody light and heavy immunoglobulin chains. The antibody titers in 96 wells after subcloning for 19 days between the hosts 3M and ISA were compared for three expression constructs, anti-IL23 (3 cDNA versions), anti-HGF, and cyno-anti-TSLP.

Figure 3:
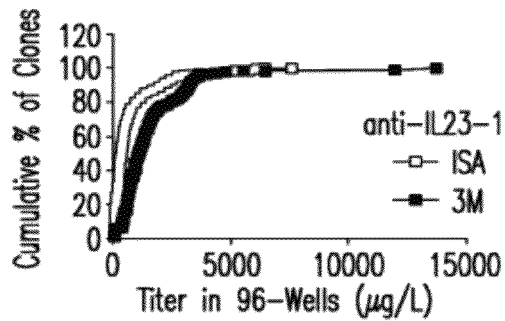
FIG. 3. Antibody titers after cloning in 96-well for 19 days after transfection for anti-IL23, cyno-anti-TSLP, and anti-HGF projects.
Figure 3:
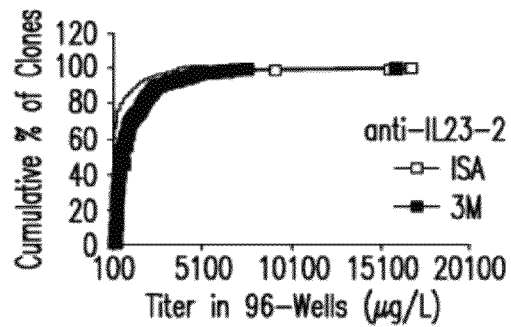
Figure 3:
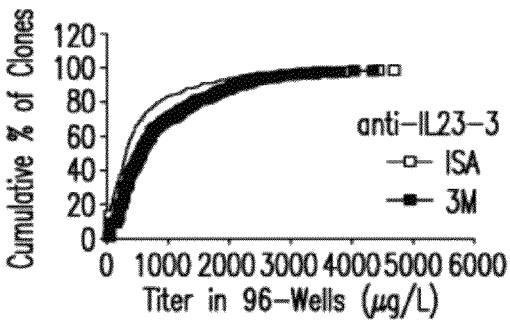
Figure 3:
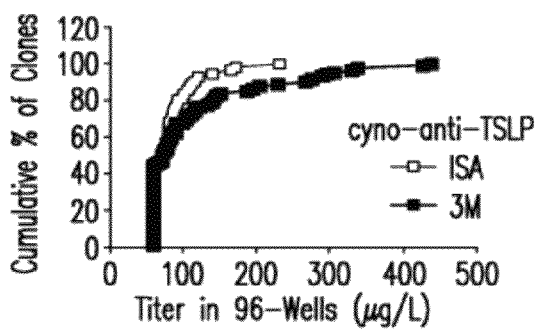
Figure 3:
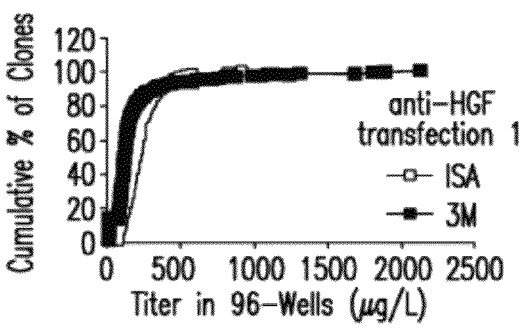
Figure 3:
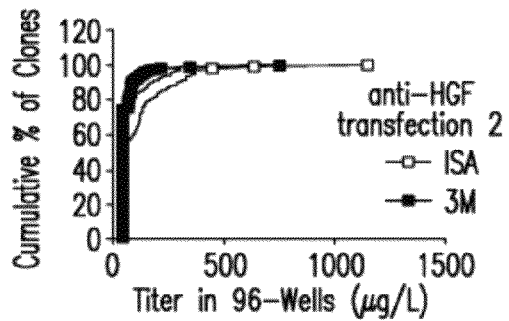

As shown in FIG. 3, in the cases of versions 2 & 3 of anti-IL-23, the titer distribution of 3M was only slightly higher than that of ISA (at the lower range). In the cases of version 1 of anti-IL23, cyno-anti-TSLP, and first transfection of anti-HGF, the titer distribution of 3M was much higher than for that of ISA. While, for the second transfection of anti-HGF, the titer distribution was reversed, i.e., ISA was slightly higher than that of 3M. Thus, the titer distribution of 3M was statistically higher than for that of ISA. However, exceptions did exist. The reason for the exceptions may be that the comparisons were done in attachment mode (i.e., wherein cells were grown in T75 flasks in adherent culture containing serum media, instead of growing in shake-flasks in suspension condition in a serum-free medium); therefore, the advantage of the robustness (obtained by serum-free suspension adaptation and cloning) of 3M may not have been evident in this subcloning stage in 96 wells.

Figure 4:
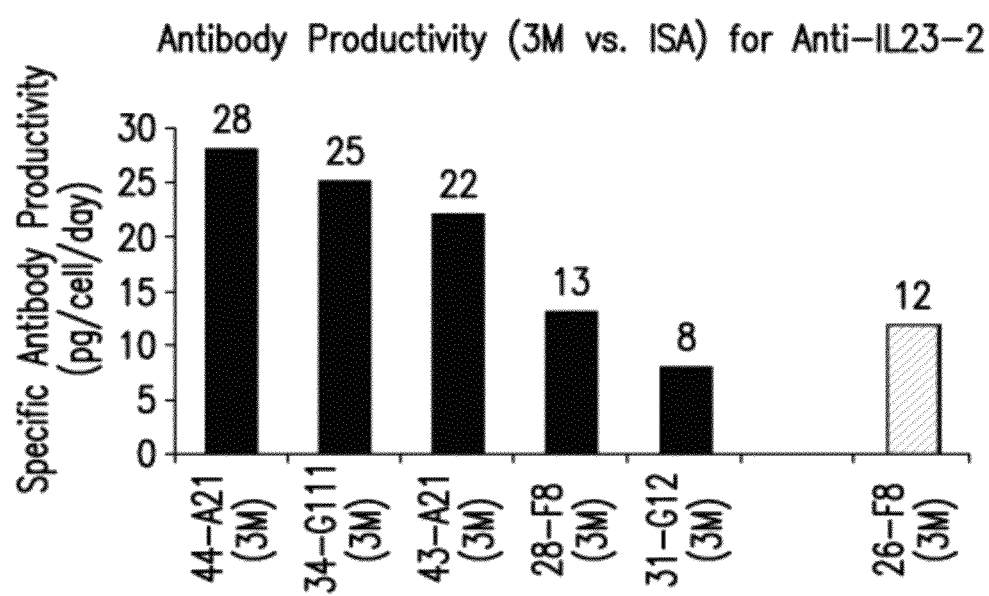
FIG. 4. Specific productivity of successful clones for anti-IL23 version 2 project.

A key comparison between 3M and ISA is in the final stage of cell line development, i.e., in serum-free suspension mode. Since, at this stage, only a limited number of clones can be selected due to their good growth and sustainable antibody productivity, we compared the number of successful clones from 3M and ISA in different projects. Successful clones were defined, here, as cell lines with good cell growth and relatively high and stable specific productivity in serum-free suspension for over 40 generations. As described below, the majority of the successful clones from three major projects were found to be derived from 3M, instead of ISA:

For anti-IL23, there were 3 versions of cDNAs tested.
1) For version 1 anti-IL23, the only successful clone was from 3M with a specific productivity of 8 pcd (picograms per cell per day) of immunoglobulin;
2) For version 2 anti-IL23, 6 out of 7 successful clones were from 3M (FIG. 4). The specific productivity in pcd for these 3M clones were 28, 25, 22, 13 and 8. One ISA clone had a specific productivity of 12 pcd of immunoglobulin, which was low compared to that of the 3M clones.
3) For version 3 anti-IL-23, all 5 successful clone were from 3M. The specific productivity in pcd of immunoglobulin for these 3M clones were 25, 21, 19, 15 and 10.

For anti-HGF, gene non-optimized and optimized versions were generated. Factors affecting mRNA stability, e.g., GC content, ribosomal binding sites, consensus and cryptic splice sites, repeats and secondary structures, were considered during gene optimization.
1) For non-optimized versions, both of 2 successful clones were from 3M. A clone from ISA grew very well in serum-free suspension, however, the specific productivity dropped down, to become negligible, in only a few generations.
2) For optimized versions, transfected cell lines did not only produce more antibodies but also were stable for longer generations.

From the observations described above, we have concluded that 3M is a superior host as compared to ISA for cell line development in producing therapeutic antibodies, immunoglobulins and other proteins, particularly proteins of therapeutic interest.

* * *

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An isolated Chinese hamster ovary cell deposited at the American Type Culture Collection under deposit number PTA-10481.

2. The cell of claim 1 in an aqueous liquid cell culture medium.

3. The cell of claim 1 in a vessel.

4. The cell of claim 1 which comprises a vector.

5. The cell of claim 4 wherein the vector comprises a polynucleotide encoding one or more proteins.

6. The cell of claim 1 comprising a protein that is an immunoglobulin comprising an amino acid sequence selected from the group consisting of SEQ ID NOs: 1-8, 21, 22, 42, 43, 58-69, 79, 80, 81, 85, 89, 93 and 101 or a mature fragment thereof or an immunoglobulin comprising one or more CDRs from said immunoglobulin; optionally linked to an immunoglobulin constant chain; or one or both chains of etanercept.

7. The cell of claim 1 comprising a protein that is an immunoglobulin chain comprising:

(1)
CDR-L1:
 (SEQ ID NO: 9)
KASKKVTIFGSISALH,

CDR-L2:

-continued

NGAKLES,
and

CDR-L3:
(SEQ ID NO: 11)
LQNKEVPYT;

(2)
CDR-H1:
(SEQ ID NO: 12)
SYGIT,

CDR-H2:
(SEQ ID NO: 13)
ENYPRSGNTYYNEKFKG,
and

CDR-H3:
(SEQ ID NO: 14)
CEFISTVVAPYYYALDY
or
(SEQ ID NO: 15)
SEFISTVVAPYYYALDY
or
(SEQ ID NO: 16)
AEFISTVVAPYYYALDY
or
(SEQ ID NO: 17)
VEFISTVVAPYYYALDY
or
(SEQ ID NO: 18)
SEFISTVMAPYYYALDY
or
(SEQ ID NO: 19)
SEFTSTVVAPYYYALDY;

(3)
CDRH1:
(SEQ ID NO: 23)
Gly Phe Thr Phe Ser Ser Tyr Thr Met Ser,

CDRH2:
(SEQ ID NO: 24)
Thr Ile Ser Ser Gly Gly Thr Tyr Thr Tyr Tyr Pro
Asp Ser Val Lys Gly,
and CDRH3:
(SEQ ID NO: 25)
Asp Asn His Ala Tyr Asp Arg Gly Pro Phe Phe Asp
Tyr;

(4)
CDRL1:
(SEQ ID NO: 26)
Lys Ser Ser Gln Asn Leu Phe Tyr Arg Ser Asn Gln
Lys Asn His Leu Ala,

CDRL2:
(SEQ ID NO: 27)
Trp Thr Ser Thr Arg Glu Ser,
and

CDRL3:
(SEQ ID NO: 28)
Gln Gln Tyr Tyr Ser Tyr Pro Pro Thr;

(5)
CDRH1:
(SEQ ID NO: 29)
Ala Tyr Gly Met Asp,

-continued

CDRH2:
(SEQ ID NO: 30)
Ser Ile Ser Pro Ser Gly Gly Arg Thr Lys Tyr Ala
Asp Ser Val Lys Gly,
and CDRH3:
(SEQ ID NO: 31)
Asp Leu Gly Gly Gly Tyr Tyr Tyr Tyr Gly Met
Asp Val;

(6)
CDRL1:
(SEQ ID NO: 32)
Thr Gly Thr Ser Ser Asp Val Gly Gly Tyr Asn Tyr
Val Ser,

CDRL2:
(SEQ ID NO: 33)
Glu Val Ser Asn Arg Pro Ser,
and

CDRL3:
(SEQ ID NO: 34)
Ser Ser Tyr Thr Ser Ser Ser Thr Leu Phe Tyr Val;

(7)
CDRH1:
(SEQ ID NO: 35)
GKTFWSWGIN,

CDRH2:
(SEQ ID NO: 36)
YIYIGTGYTEPNPKYKG,
and

CDRH3:
(SEQ ID NO: 37)
IGGYYGNFAD
or
(SEQ ID NO: 38)
IGGYYGNFDQ;

(8)
CDRL1:
(SEQ ID NO: 39)
RSSQSLLISGGNTYLN,

CDRL2:
(SEQ ID NO: 40)
LVSKLDQ,
and

CDRL3:
(SEQ ID NO: 41)
WQGTYFPLT;

(9)
CDRH1:
(SEQ ID NO: 44)
TYWMH
or
(SEQ ID NO: 45)
TYWMH,

CDRH2:
(SEQ ID NO: 46)
EINPTNGHTNYNEKFKS,
(SEQ ID NO: 47)
EINPTNGHTNYNPSFQG,
or
(SEQ ID NO: 48)
EINPTNGHTNYNQKFQG,
and

```
CDRH3:
                                       (SEQ ID NO: 49)
NYVGSIFDY
or
                                       (SEQ ID NO: 50)
NYVGSIFDY;

(10)
CDRL1:
                                       (SEQ ID NO: 51)
KASENVVSYVS
or
                                       (SEQ ID NO: 52)
KASENVVSYVS,

CDRL2:
                                       (SEQ ID NO: 53)
GASNRNT, (SEQ ID NO: 54)
GASNRNT
or
                                       (SEQ ID NO: 55)
GASNRES,
and CDRL3:
                                       (SEQ ID NO: 56)
GQSYNYPYT
or
                                       (SEQ ID NO: 57)
GQSYNYPYT;

(11)
CDRH1:
                                       (SEQ ID NO: 82)
GYTFSSYGMY;

CDRH2:
                                       (SEQ ID NO: 83)
WIDPGSGGTKYNEKFKG;
and

CDRH3:
                                       (SEQ ID NO: 84)
ERYGYYFDY;

(12)
CDRL1:
                                       (SEQ ID NO: 86)
RASQYVGSYLN;

CDRL2:
                                       (SEQ ID NO: 87)
DASNRAT;
and

CDRL3:
                                       (SEQ ID NO: 88)
QVWDSSPPVV;

(13)
CDRL1:
                                       (SEQ ID NO: 90)
RASQDVSRYLT;

CDRL2:
                                       (SEQ ID NO: 91)
AASSLQS;
and

CDRL3:
                                       (SEQ ID NO: 92)
QAYDYSLSGYV;

(14)
```

```
CDRH1:
                                       (SEQ ID NO: 94)
GYTFSSYWMH;

CDRH2:
                                       (SEQ ID NO: 95)
RIDPYNGGTKYNEKFKG;
and

CDRH3:
                                       (SEQ ID NO: 96)
YGYYLGSYAMDY;

(15)
CDRH1:
                                       (SEQ ID NO: 98)
GYTFTDYYMN;

CDHR2:
                                       (SEQ ID NO: 99)
DINPNNGGAIYNQKFKG;
and CDRH3:
                                       (SEQ ID NO: 100)
GIITEIAEDF;
or

(16)
CDRL1:
                                       (SEQ ID NO: 102)
KASQNVGTNVV;

CDRL2:
                                       (SEQ ID NO: 103)
SASYRYS;
and

CDRL3:
                                       (SEQ ID NO: 104)
QQYKTYPYT;
``` optionally linked to an immunoglobulin constant chain.

8. A method for making one or more polypeptides; or antibodies or antigen-binding fragments thereof that comprise said polypeptides; comprising introducing one or more polynucleotides encoding said polypeptides into the cell of claim 1 and culturing the cell in conditions under which the polypeptides are produced.

9. The method of claim 8 further comprising isolating the polypeptide.

10. The method of claim 8 wherein the polypeptide is an immunoglobulin.

11. The method of claim 10 wherein the immunoglobulin comprises an amino acid sequence selected from the group consisting of SEQ ID NOs: 1-8, 21, 22, 42, 43, 58-69, 79, 80, 81, 85, 89, 93 and 101 or a mature fragment thereof or an immunoglobulin comprising one or more CDRs from said immunoglobulin; optionally linked to an immunoglobulin constant chain.

12. The method of claim 10 wherein the immunoglobulin comprises:

```
(1)
CDR-L1:
                                       (SEQ ID NO: 9)
KASKKVTIFGSISALH,

CDR-L2:
                                       (SEQ ID NO: 10)
NGAKLES,
and

CDR-L3:
```

LQNKEVPYT; (SEQ ID NO: 11)

(2)
CDR-H1: (SEQ ID NO: 12)
SYGIT,

CDR-H2: (SEQ ID NO: 13)
ENYPRSGNTYYNEKFKG,
and

CDR-H3: (SEQ ID NO: 14)
CEFISTVVAPYYYALDY
or

SEFISTVVAPYYYALDY (SEQ ID NO: 15)
or

AEFISTVVAPYYYALDY (SEQ ID NO: 16)
or

VEFISTVVAPYYYALDY (SEQ ID NO: 17)
or

SEFISTVMAPYYYALDY (SEQ ID NO: 18)
or

SEFTSTVVAPYYYALDY; (SEQ ID NO: 19)

(3)
CDRH1: (SEQ ID NO: 23)
Gly Phe Thr Phe Ser Ser Tyr Thr Met Ser,

CDRH2: (SEQ ID NO: 24)
Thr Ile Ser Ser Gly Gly Thr Tyr Thr Tyr Tyr Pro Asp Ser Val Lys Gly,
and CDRH3: (SEQ ID NO: 25)
Asp Asn His Ala Tyr Asp Arg Gly Pro Phe Phe Asp Tyr;

(4)
CDRL1: (SEQ ID NO: 26)
Lys Ser Ser Gln Asn Leu Phe Tyr Arg Ser Asn Gln Lys Asn His Leu Ala,

CDRL2: (SEQ ID NO: 27)
Trp Thr Ser Thr Arg Glu Ser,
and

CDRL3: (SEQ ID NO: 28)
Gln Gln Tyr Tyr Ser Tyr Pro Pro Thr;

(5)
CDRH1: (SEQ ID NO: 29)
Ala Tyr Gly Met Asp,

CDRH2: (SEQ ID NO: 30)
Ser Ile Ser Pro Ser Gly Gly Arg Thr Lys Tyr Ala Asp Ser Val Lys Gly,
and CDRH3: (SEQ ID NO: 31)
Asp Leu Gly Gly Gly Tyr Tyr Tyr Tyr Gly Met Asp Val;

(6)
CDRL1: (SEQ ID NO: 32)
Thr Gly Thr Ser Ser Asp Val Gly Gly Tyr Asn Tyr Val Ser,

CDRL2: (SEQ ID NO: 33)
Glu Val Ser Asn Arg Pro Ser,
and

CDRL3: (SEQ ID NO: 34)
Ser Ser Tyr Thr Ser Ser Ser Thr Leu Phe Tyr Val;

(7)
CDRH1: (SEQ ID NO: 35)
GKTFWSWGIN,

CDRH2: (SEQ ID NO: 36)
YIYIGTGYTEPNPKYKG,
and

CDRH3: (SEQ ID NO: 37)
IGGYYGNFAD
or

IGGYYGNFDQ; (SEQ ID NO: 38)

(8)
CDRL1: (SEQ ID NO: 39)
RSSQSLLISGGNTYLN,

CDRL2: (SEQ ID NO: 40)
LVSKLDQ,
and

CDRL3: (SEQ ID NO: 41)
WQGTYFPLT;

(9)
CDRH1: (SEQ ID NO: 44)
TYWMH
or

TYWMH, (SEQ ID NO: 45)

CDRH2: (SEQ ID NO: 46)
EINPTNGHTNYNEKFKS,

EINPTNGHTNYNPSFQG, (SEQ ID NO: 47)
or

EINPTNGHTNYNQKFQG, (SEQ ID NO: 48)
and

CDRH3: (SEQ ID NO: 49)
NYVGSIFDY
or

NYVGSIFDY; (SEQ ID NO: 50)

(10)
CDRL1:
KASENVVSYVS (SEQ ID NO: 51)
or

KASENVVSYVS, (SEQ ID NO: 52)

CDRL2:
GASNRNT, (SEQ ID NO: 53)

GASNRNT (SEQ ID NO: 54)
or

GASNRES, (SEQ ID NO: 55)
and

CDRL3:
GQSYNYPYT (SEQ ID NO: 56)
or

GQSYNYPYT; (SEQ ID NO: 57)

(11)
CDRH1:
GYTFSSYGMY; (SEQ ID NO: 82)

CDRH2:
WIDPGSGGTKYNEKFKG; (SEQ ID NO: 83)
and

CDRH3:
ERYGYYFDY; (SEQ ID NO: 84)

(12)
CDRL1:
RASQYVGSYLN; (SEQ ID NO: 86)

CDRL2:
DASNRAT; (SEQ ID NO: 87)
and

CDRL3:
QVWDSSPPVV; (SEQ ID NO: 88)

(13)
CDRL1:
RASQDVSRYLT; (SEQ ID NO: 90)

CDRL2:
AASSLQS; (SEQ ID NO: 91)
and

CDRL3:
QAYDYSLSGYV; (SEQ ID NO: 92)

(14)
CDRH1:
GYTFSSYWMH; (SEQ ID NO: 94)

CDRH2:
RIDPYNGGTKYNEKFKG; (SEQ ID NO: 95)
and

CDRH3:
YGYYLGSYAMDY; (SEQ ID NO: 96)

(15)
CDRH1:
GYTFTDYYMN; (SEQ ID NO: 98)

CDHR2:
DINPNNGGAIYNQKFKG; (SEQ ID NO: 99)
and

CDRH3:
GIITEIAEDF; (SEQ ID NO: 100)
or

(16)
CDRL1:
KASQNVGTNVV; (SEQ ID NO: 102)

CDRL2:
SASYRYS; (SEQ ID NO: 103)
and

CDRL3:
QQYKTYPYT; (SEQ ID NO: 104)

optionally linked to an immunoglobulin constant chain.

13. The method of claim 10 wherein the immunoglobulin is a light chain immunoglobulin linked to a kappa or lambda constant immunoglobulin chain and/or wherein the immunoglobulin is a heavy chain immunoglobulin linked to a gamma-1, gamma-2, gamma-3 or gamma-4 constant immunoglobulin chain.

14. A method for producing an antibody comprising inoculating an initial mammalian cell growth medium, pre-warmed to about 37° C.; which initial medium comprises HEPES, sodium bicarbonate buffers, inorganic salts, non-essential amino acids, recombinant human insulin, trace elements and surfactants; and which does not comprise L-glutamine, antibiotics, antimycotics or animal-derived components; with one or more cells of claim 1 expressing the antibody light chain immunoglobulin and heavy chain immunoglobulin, to a cell density of about $2.5-5\times10^5$ cells/ml; and, adding the following supplements to the medium before, simultaneously with or immediately after said inoculation:

soy hydrolysate to a final concentration of about 10 g/liter; and, optionally, an amino acid feed wherein the concentration of the components added by said amino acid feed are approximately those set forth below:

| | |
|---|---|
| L-arginine: | 126.4 mg/liter |
| L-cystine: | 34 mg/liter |
| L-histidine: | 42 mg/liter |
| L-isoleucine: | 52 mg/liter |
| L-leucine: | 52 mg/liter |
| L-lysine: | 72 mg/liter |
| L-Methionine: | 15.2 mg/liter |
| L-phenylalanine: | 33 mg/liter |
| L-threonine: | 47.6 mg/liter |
| L-tryptophan: | 10.2 mg/liter |
| L-tyrosine: | 36 mg/liter |
| L-valine: | 46.8 mg/liter |
| L-alanine: | 8.9 mg/liter |

-continued

| | |
|---|---|
| L-asparagine: | 30 mg/liter |
| L-aspartic acid: | 26.6 mg/liter |
| L-glutamic acid: | 29.4 mg/liter |
| glycine: | 15 mg/liter |
| L-proline: | 23 mg/liter |
| L-serine: | 21 mg/liter; | and, when viable cell density reaches over about $1.2 \times 10^6$ cells/ml, adding supplement feeds wherein the concentration of the components added by said supplement feeds are approximately those set forth below:

| | |
|---|---|
| Sodium selenite: | 0.01426 mg/liter |
| Adenine sulfate: | 1.632 mg/liter |
| Adenosine: | 17.6 mg/liter |
| Cytidine: | 17.6 mg/liter |
| Guanosine: | 17.6 mg/liter |
| Uridine: | 17.6 mg/liter |
| Hypoxanthine: | 11.8 mg/liter |
| L-citrulline: | 12.6 mg/liter |
| L-ornithine-HCl: | 25.6 mg/liter |
| Biotin: | 0.28 mg/liter |
| Flavin Adenine Dinucleotide: | 0.05 mg/liter |
| Folic Acid: | 4.6 mg/liter |
| Lipoic Acid: | 0.52 mg/liter |
| Niacin: | 31.4 mg/liter |
| Pyridoxine HCl: | 3 mg/liter |
| Riboflavin: | 1.86 mg/liter |
| Thiamine HCl: | 16 mg/liter |
| Vitamin E: | 0.376 mg/liter |
| Vitamin B12: | 3.4 mg/liter |
| Choline Chloride: | 50.2 mg/liter |
| Ethanolamine HCl: | 4.4 mg/liter |
| i-Inositol: | 73.2 mg/liter |
| Thymidine: | 7.8 mg/liter |
| Putrescine 2HCl: | 0.4 mg/liter |
| Progesterone: | 0.015 mg/liter |
| D-Calcium Pantothenate: | 23.8 mg/liter |
| L-asparagine: | 812 mg/liter |
| L-proline | 216 mg/liter |
| L-isoleucine | 370 mg/liter |
| L-cysteine-HCl | 224 mg/liter |
| L-leucine | 332 mg/liter |
| L-threonine | 164 mg/liter |
| L-tyrosine | 198 mg/liter |
| L-arginine | 186 mg/liter |
| L-aspartic acid | 71 mg/liter |
| L-glutamic acid | 126 mg/liter |
| Glycine | 57 mg/liter |
| L-histidine | 125 mg/liter |
| L-methionine | 132 mg/liter |
| L-tryptophan | 99 mg/liter |
| L-lysine | 293 mg/liter |
| L-phenylalanine | 174 mg/liter |
| L-valine | 262 mg/liter |
| L-serine: | 260 mg/liter |
| Sodium phosphate monobasic: | 288.2 mg/liter |
| Zinc sulfate: | 1.08 mg/liter |
| Cupric sulfate: | 0.0032 mg/liter |
| Ammonium vanadate: | 0.00078 mg/liter |
| Cobalt chloride: | 0.0025 mg/liter |
| Nickel dichloride hexahydrate: | 0.0004 mg/liter |
| Sodium molybdate dehydrate: | 0.00016 mg/liter; | and, maintaining glucose concentration in the medium at about 1.5 g/liter and maintaining L-glutamine concentration in the medium at about 150 mg/liter; and during cell growth maintaining $O_2$ concentration at about 60%; pH at about 6.8±0.02 and temperature at about 36.5° C.±0.5° C.; and, optionally, removing the host cells from the medium when cell viability is below about 60%.

15. The method of claim 14 further comprising recovering the culture medium from the cells by disk-stack centrifuging the medium, depth filtering the medium and filtering the medium through a filter with about a 0.2 micron pore size.

16. The method of claim 14 further comprising purifying the immunoglobulins from the medium by column chromatographic fractionation.

17. A master cell bank or working cell bank comprising the cell of claims 1.

18. The cell of claim 1 in a cell freezing medium.

19. The cell of claim 18 wherein the cell freezing medium comprises dimethylsulfoxide.

20. A method for making a Chinese hamster ovary cell comprising adapting CHO-DXB11 cells into animal-component free medium in suspension for 83 days; then subcloning the cells into said medium twice.

* * * * *